US005679550A

United States Patent [19]

Yoshimura et al.

[11] Patent Number: 5,679,550

[45] Date of Patent: Oct. 21, 1997

[54] HST-2 MUTEINS, PHARMACEUTICAL COMPOSITIONS AND KITS COMPRISING SAME, AND PREPARATION OF SAME

[75] Inventors: Koji Yoshimura; Kaori Ishimaru, both of Osaka; Koichi Igarashi, Kyoto; Masaaki Terada, Tokyo, all of Japan

[73] Assignees: Takeda Chemical Industries, Inc., Osaka; President of National Cancer Center, Tokoyo, both of Japan

[21] Appl. No.: 551,171

[22] Filed: Oct. 31, 1995

Related U.S. Application Data

[63] Continuation of Ser. No. 196,001, Feb. 10, 1994, abandoned.

[30] Foreign Application Priority Data

| | | | |
|---|---|---|---|
| Feb. 12, 1993 | [JP] | Japan | 5-024399 |
| Jul. 28, 1993 | [JP] | Japan | 5-186507 |

[51] Int. Cl.$^6$ ........................ A61K 38/17; C07K 14/435; C12N 15/12

[52] U.S. Cl. ........................ 435/69.1; 530/397; 530/350; 530/380; 435/69.1; 435/172.3; 514/2; 514/8; 514/12

[58] Field of Search .................................... 530/399, 397, 530/350, 380; 435/69.1, 172.3; 514/2, 8, 12

[56] References Cited

FOREIGN PATENT DOCUMENTS

| | | |
|---|---|---|
| A-421455 | 4/1991 | European Pat. Off. . |
| A-0488196 | 6/1992 | European Pat. Off. . |
| A-0503297 | 9/1992 | European Pat. Off. . |

OTHER PUBLICATIONS

Oncogene, vol. 4, No. 3, "Characterization of the HST–related FGF.6 Gene, a new member of the fibroblast growth factor gene family", pp. 335–340, Mar. 1989, Marics, I., et al.

Oncogene, vol. 7, No. 2, "Human hst–2 (FGF–6) oncogene: cDNA cloning and Characterization", pp. 303–309, 1992, Iida, S., et al.

Mol. Cell Biol., vol. 13, No. 7, "Molecular Cloning of Novel Cytokine cDNA Encoding the Ninth Member of the Fibroblast Growth Factor Family, Which has a Unique Secretion Property", pp. 4251–4259, Jul. 1993, Miyamoto, M., et al.

*Primary Examiner*—Vasu S. Jagannathan
*Assistant Examiner*—Elizabeth C. Kemmerer
*Attorney, Agent, or Firm*—David G. Conlin; Ronald I. Eisenstein

[57] ABSTRACT

The present invention provides a polypeptide represented by the following amino acid sequence:

$(Met)_n$X Leu Ala Gly Glu Ile Ala Gly Val Asn Trp Glu Ser

Gly Tyr Leu Val Gly Ile Lys Arg Gln Arg Arg Leu Tyr Cys Asn

Val Gly Ile Gly Phe His Leu Gln Val Leu Pro Asp Gly Arg Ile

Ser Gly Thr His Glu Glu Asn Pro Tyr Ser Leu Leu Glu Ile Ser

Thr Val Glu Arg Gly Val Val Ser Leu Phe Gly Val Arg Ser Ala

Leu Phe Val Ala Met Asn Ser Lys Gly Arg Leu Tyr Ala Thr Pro

Ser Phe Gln Glu Glu Cys Lys Phe Arg Glu Thr Leu Leu Pro Asn

Asn Tyr Asn Ala Tyr Glu Ser Asp Leu Tyr Gln Gly Thr Tyr Ile

Ala Leu Ser Lys Tyr Gly Arg Val Lys Arg Gly Ser Lys Val Ser

Pro Ile Met Thr Val Thr His Phe Leu Pro Arg Ile wherein n is 0 or 1 and X represents Pro Ala Gly Thr Arg Ala Asn Asn Thr Leu Leu Asp Ser Arg Gly Trp Gly Thr Leu Leu Ser Arg Ser Arg Ala Gly or a fragment thereof (n=0: SEQ ID NO:1, n=1: SEQ ID NO:2), a recombinant DNA coding for the polypeptide, a vector containing the recombinant DNA, the preparation of a transformant carrying the vector, and the production of the polypeptide with the transformant. The use of this peptide in pharmaceutical compositions is also provided.

10 Claims, 9 Drawing Sheets

```
                                      10                                       20
Met Ala Leu Gly Gln Lys Leu Phe Ile Thr Met Ser Arg Gly Ala Gly Arg Leu Gln Gly
                                      30                                       40
Thr Leu Trp Ala Leu Val Phe Leu Gly Ile Leu Val Gly Met Val Val Pro Ser Pro Ala
                                      50                                       60
Gly Thr Arg Ala Asn Asn Thr Leu Leu Asp Ser Arg Gly Trp Gly Thr Leu Leu Ser Arg
                                      70                                       80
Ser Arg Ala Gly Leu Ala Gly Glu Ile Ala Gly Val Asn Trp Glu Ser Gly Tyr Leu Val
                                      90                                      100
Gly Ile Lys Arg Gln Arg Arg Leu Tyr Cys Asn Val Gly Ile Gly Phe His Leu Gln Val
                                     110                                      120
Leu Pro Asp Gly Arg Ile Ser Gly Thr His Glu Glu Asn Pro Tyr Ser Leu Leu Glu Ile
                                     130                                      140
Ser Thr Val Glu Arg Gly Val Val Ser Leu Phe Gly Val Arg Ser Ala Leu Phe Val Ala
                                     150                                      160
Met Asn Ser Lys Gly Arg Leu Tyr Ala Thr Pro Ser Phe Gln Glu Glu Cys Lys Phe Arg
                                     170                                      180
Glu Thr Leu Leu Pro Asn Asn Tyr Asn Ala Tyr Glu Ser Asp Leu Tyr Gln Gly Thr Tyr
                                     190                                      200
Ile Ala Leu Ser Lys Tyr Gly Arg Val Lys Arg Gly Ser Lys Val Ser Pro Ile Met Thr

Val Thr His Phe Leu Pro Arg Ile
```

FIG. 1

```
                                        10                                      20
Met Pro Ala Gly Thr Arg Ala Asn Asn Thr Leu Leu Asp Ser Arg Gly Trp Gly Thr Leu
                                        30                                      40
Leu Ser Arg Ser Arg Ala Gly Leu Ala Gly Glu Ile Ala Gly Val Asn Trp Glu Ser Gly
                                        50                                      60
Tyr Leu Val Gly Ile Lys Arg Gln Arg Arg Leu Tyr Cys Asn Val Gly Ile Gly Phe His
                                        70                                      80
Leu Gln Val Leu Pro Asp Gly Arg Ile Ser Gly Thr His Glu Glu Asn Pro Tyr Ser Leu
                                        90                                     100
Leu Glu Ile Ser Thr Val Glu Arg Gly Val Val Ser Leu Phe Gly Val Arg Ser Ala Leu
                                       110                                     120
Phe Val Ala Met Asn Ser Lys Gly Arg Leu Tyr Ala Thr Pro Ser Phe Gln Glu Glu Cys
                                       130                                     140
Lys Phe Arg Glu Thr Leu Leu Pro Asn Asn Tyr Asn Ala Tyr Glu Ser Asp Leu Tyr Gln
                                       150                                     160
Gly Thr Tyr Ile Ala Leu Ser Lys Tyr Gly Arg Val Lys Arg Gly Ser Lys Val Ser Pro
                                       170
Ile Met Thr Val Thr His Phe Leu Pro Arg Ile
```

FIG. 2

```
                                    10                                      20
Met Gly Leu Ala Gly Glu Ile Ala Gly Val Asn Trp Glu Ser Gly Tyr Leu Val Gly Ile
                                    30                                      40
Lys Arg Gln Arg Arg Leu Tyr Cys Asn Val Gly Ile Gly Phe His Leu Gln Val Leu Pro
                                    50                                      60
Asp Gly Arg Ile Ser Gly Thr His Glu Glu Asn Pro Tyr Ser Leu Leu Glu Ile Ser Thr
                                    70                                      80
Val Glu Arg Gly Val Val Ser Leu Phe Gly Val Arg Ser Ala Leu Phe Val Ala Met Asn
                                    90                                     100
Ser Lys Gly Arg Leu Tyr Ala Thr Pro Ser Phe Gln Glu Glu Cys Lys Phe Arg Glu Thr
                                   110                                     120
Leu Leu Pro Asn Asn Tyr Asn Ala Tyr Glu Ser Asp Leu Tyr Gln Gly Thr Tyr Ile Ala
                                   130                                     140
Leu Ser Lys Tyr Gly Arg Val Lys Arg Gly Ser Lys Val Ser Pro Ile Met Thr Val Thr

His Phe Leu Pro Arg Ile
```

FIG. 4

HST-2 MUTEINS, PHARMACEUTICAL COMPOSITIONS AND KITS COMPRISING SAME, AND PREPARATION OF SAME

This is a continuation of application Ser. No. 08/196,001 filed on Feb. 10, 1994, now abandoned.

FIELD OF THE INVENTION

The present invention relates to a polypeptide having a heparin-binding secretory transforming factor 2 activity (hereinafter also briefly referred to as hst-2 in this specification) such as growth promoting activity on animal cells, a recombinant DNA coding for the same, and a method for preparing said polypeptide and a pharmaceutical composition containing said polypeptide. The present invention also relates to a method for promoting an increase in the number of platelets in a mammal using hst-2.

BACKGROUND OF THE INVENTION

Groups of cell growth factors belonging to the heparin-binding growth factor (HBGF) family show homology with one another on amino acid sequences and are commonly characterized by strong heparin-binding activity. The cell growth factors belonging to this family include acidic and basic fibroblast growth factors (aFGF and bFGF), hst-1, INT2, FGF5 and keratinocyte growth factor (KGF). Of these cell growth factors, there is a report that FGF has activity on various cells and particularly has growth promoting activity and differentiation promoting activity on mesodermal cells [Gospodarowicz et al., *J. Cell. Physiol., supplt.,* 5, 15 (1987)]. FGF has also been investigated for application to drugs for promoting wound healing, or repair of the cardiac muscle or the nervous tissue after ischemia.

An hst-1 gene is a transforming gene identified by a focus forming method, and a product thereof has cell growth promoting activity and anglogenesis inducing activity in vivo (Japanese Unexamined Patent Publication No. 3-218398: European Patent Publication No. 421455) as well as FGF. An hst-2 gene was identified as a gene having high homology with the hst-1 gene by a DNA blot hybridization method [Sakamoto et al., *Biochem. Biophys. Res. Commun.,* 151, 965 (1988)]. The same gene was also reported as an FGF6 gene [Marics I. et al., Oncogene, 4, 335(1989) and Coulier F. et al., Oncogene 6(4), 1433(1991)]. They also report that the FGF6 gene codes three in frame ATG codons which are able to initiate the translation of three peptides of 175, 198 and 208 residues. Further, hst-2 was considered by the present inventors to actually have biological activity and to be a novel growth factor belonging to the HST family, because hst-2 gene-introduced fibroblasts formed tumors on nude mice [Naito et al., *Jpn. J. Cancer Res. Abstr.,* 500 (1989)]. Products of the hst-2 genes have therefore also been expected to be applicable to drugs as promoters for wound healing, or repair of the cardiac muscle after cardiac ischemia and the nervous tissue after brain ischemia.

In order to promote the investigation of the hst-2 protein, it is necessary to obtain the protein in large amounts and in high purity. In *Oncogene,* 5, 823 (1990), de Lapeyriere et al. reported that the protein having growth promoting activity on the animal cells was possibly localized in the muscles or the testes. The leukemia cell line HEL [Martin and Papayannoponlou, *Science,* 216, 1223 (1982)] or CMK [Sato et al., *British Journal of Hematology,* 72, 184 (1989)] which possibly produces the peptide has been reported. The isolation and purification of the protein from such sources are complicated and the desired protein has heretofore been obtained only in small amounts. Accordingly, a method for obtaining the hst-2 protein in large amounts and in high purity has been earnestly desired.

For the hst-2 gene, the nucleotide sequence thereof has recently been reported [S. Iida et al., *Oncogene,* 7, 303 (1992) and European Patent Publication No. 421455], and these reports also provide constituent amino acids deduced therefrom. However, a method for producing hst-2 by the use of recombinant technology has not been reported.

Although some of the properties and biological activity of hst-2 remain to be studied, as described above, the application of hst-2 to drugs and reagents has generally been expected. However, it has hitherto been impossible to obtain sufficient amounts of hst-2 as described above, which has hindered investigation and development.

SUMMARY OF THE INVENTION

In accordance with the present invention, hst-2 has been modified so as to be microbiologically produced in large amounts without adverse effect on the activity thereof by the use of the recombinant DNA technique. Such modification is considered to possibly result in not only an increase in production ability of hst-2 in cells, but also increases in stability and cell growth activity per molecule of hst-2 and further activation of unknown biological activity.

The present inventors have prepared mutein genes partly lacking hst-2 genes and expressed the mutein genes in microorganisms by recombinant DNA techniques in order to conduct intensive investigation of increases in the production ability of hst-2 in cells and activity, and changes in biological activity, and have discovered thus prepared polypeptides serving these purposes. Further investigation based on these findings led to completion of the present invention.

The present invention is a polypeptide having a specific range of amino acid sequence of hst-2, namely wherein said polypeptide is lacking the first 38 to 63 amino acid residues from the N-terminus of SEQ ID NO:6 and a novel use of hst-2. More specifically, the present invention provides:

(1) A polypeptide represented by the following amino acid sequence:

(Met)$_n$X Leu Ala Gly Glu Ile Ala Gly Val Asn Trp Glu Ser

Gly Tyr Leu Val Gly Ile Lys Arg Gln Arg Arg Leu Tyr Cys Asn

Val Gly Ile Gly Phe His Leu Gln Val Leu Pro Asp Gly Arg Ile

Ser Gly Thr His Glu Glu Asn Pro Tyr Ser Leu Leu Glu Ile Ser

Thr Val Glu Arg Gly Val Val Ser Leu Phe Gly Val Arg Ser Ala

Leu Phe Val Ala Met Asn Ser Lys Gly Arg Leu Tyr Ala Thr Pro

Ser Phe Gln Glu Glu Cys Lys Phe Arg Glu Thr Leu Leu Pro Asn

Asn Tyr Asn Ala Tyr Glu Ser Asp Leu Tyr Gln Gly Thr Tyr Ile

Ala Leu Ser Lys Tyr Gly Arg Val Lys Arg Gly Ser Lys Val Ser

Pro Ile Met Thr Val Thr His Phe Leu Pro Arg Ile wherein n is 0 or 1 and X represents Pro Ala Gly Thr Arg Ala Asn Asn Thr Leu Leu Asp Ser Arg Gly Trp Gly Thr Leu Leu Ser Arg Ser Arg Ala Gly or a fragment thereof (n=0: SEQ ID NO:1, n=1: SEQ ID NO:2) hereinafter sometimes abbreviated to polypeptide (I);

(2) The polypeptide of the above (1), wherein X represents Pro Ala Gly Thr Arg Ala Asn Asn Thr Leu Leu Asp Ser Arg Gly Trp Gly Thr Leu Leu Ser Arg Ser Arg Ala Gly (n=0: SEQ ID NO:1, n=1: SEQ ID NO:2);

(3) The polypeptide of the above (1), wherein X represents Gly (n=0: SEQ ID NO:3, n=1: SEQ ID NO:4);

(4) The polypeptide of the above (1), wherein said polypeptide has amino acid sequence of SEQ ID NO:1;

(5) The mutein of the above (1), wherein said polypeptide has amino acid sequence of SEQ ID NO:3;

(6) The polypeptide of the above (1), wherein said polypeptide has a heparin-binding secretory transforming factor 2 (hst-2) activity;

(7) A recombinant DNA encoding the mutein in any one of the above (1) to (6);

(8) A vector containing the recombinant DNA of the above (7);

(9) A transformant carrying the vector of the above (8);

(10) A method of producing a polypeptide represented by the following amino acid sequence:

(Met)$_n$X Leu Ala Gly Glu Ile Ala Gly Val Asn Trp Glu Ser

Gly Tyr Leu Val Gly Ile Lys Arg Gln Arg Arg Leu Tyr Cys Asn

Val Gly Ile Gly Phe His Leu Gln Val Leu Pro Asp Gly Arg Ile

Ser Gly Thr His Glu Glu Asn Pro Tyr Ser Leu Leu Glu Ile Ser

Thr Val Glu Arg Gly Val Val Ser Leu Phe Gly Val Arg Ser Ala

Leu Phe Val Ala Met Asn Ser Lys Gly Arg Leu Tyr Ala Thr Pro

Ser Phe Gln Glu Glu Cys Lys Phe Arg Glu Thr Leu Leu Pro Asn

Asn Tyr Asn Ala Tyr Glu Ser Asp Leu Tyr Gln Gly Thr Tyr Ile

Ala Leu Ser Lys Tyr Gly Arg Val Lys Arg Gly Ser Lys Val Ser

Pro Ile Met Thr Val Thr His Phe Leu Pro Arg Ile wherein n is 0 or 1 and X represents Pro Ala Gly Thr Arg Ala Asn Asn Thr Leu Leu Asp Ser Arg Gly Trp Gly Thr Leu Leu Ser Arg Ser Arg Ala Gly or a fragment thereof (n=0: SEQ ID NO:1, n=1: SEQ ID NO:2), which comprises cultivating the transformant of the above (9) in a medium and harvesting said polypeptide from the culture broth;

(11) A pharmaceutical composition comprising an effective amount of the polypeptide in any one of the above (1) to (6) and a pharmacologically acceptable carrier;

(12) The pharmaceutical composition of the above (11), wherein said composition is a composition for promoting an increase in the number of platelets in a mammal;

(13) A method for promoting an increase in the number of platelets in a mammal which comprises administering to the mammal an effective amount of polypeptide having a heparin-binding secretory transforming factor 2 (hst-2) activity;

(14) The method of the above (13), wherein said polypeptide represents the following amino acid sequence:

(Met)$_n$Y Leu Ala Gly Glu Ile Ala Gly Val Asn Trp Glu Ser

-continued

Gly Tyr Leu Val Gly Ile Lys Arg Gln Arg Arg Leu Tyr Cys Asn

Val Gly Ile Gly Phe His Leu Gln Val Leu Pro Asp Gly Arg Ile

Ser Gly Thr His Glu Glu Asn Pro Tyr Ser Leu Leu Glu Ile Ser

Thr Val Glu Arg Gly Val Val Ser Leu Phe Gly Val Arg Ser Ala

Leu Phe Val Ala Met Asn Ser Lys Gly Arg Leu Tyr Ala Thr Pro

Ser Phe Gln Glu Glu Cys Lys Phe Arg Glu Thr Leu Leu Pro Asn

Asn Tyr Asn Ala Tyr Glu Ser Asp Leu Tyr Gln Gly Thr Tyr Ile

Ala Leu Ser Lys Tyr Gly Arg Val Lys Arg Gly Ser Lys Val Ser

Pro Ile Met Thr Val Thr His Phe Leu Pro Arg Ile wherein n is 0 or 1 and Y represents Ala Leu Gly Gln Lys Leu Phe Ile Thr Met Ser Arg Gly Ala Gly Arg Leu Gln Gly Thr Leu Trp Ala Leu Val Phe Leu Gly Ile Leu Val Gly Met Val Val Pro Ser Pro Ala Gly Thr Arg Ala Asn Asn Thr Leu Leu Asp Ser Arg Gly Trp Gly Thr Leu Leu Ser Arg Ser Arg Ala Gly or a fragment thereof (n=0: SEQ ID NO:5, n=1: SEQ ID NO:6);

(15) The method of the above (14), wherein Y represents Val Val Pro Ser Pro Ala Gly Thr Arg Ala Asn Asn Thr Leu Leu Asp Ser Arg Gly Trp Gly Thr Leu Leu Ser Arg Ser Arg Ala Gly (n=0: SEQ ID NO:7, n=1: SEQ ID NO:8) or a fragment thereof;

(16) The method of the above (13), wherein said polypeptide is polypeptide in any one of the above (1) to (6);

(17) The method of the above (13), wherein said polypeptide is administered with another agent;

(18) The method of the above (17), wherein said another agent is an anticancer agent;

(19) The method of the above (18), wherein said method comprises administering to the mammal the polypeptide and anticancer agent separately; and

(20) A kit of pharmaceutical preparations for increasing platelets and treating a disease in a mammal, which sets a pharmaceutical prepration of the polypeptide in any one of the above (1) to (6) and an anticancer agent.

BRIEF DESCRIPTION OF THE DRAWINGS

FIG. 1 shows an amino acid sequence (SEQ ID NO:6) deduced from a coding region of hst-2 containing a leader sequence constituting an open reading frame of hst-2 cDNA;

FIG. 2 shows an amino acid sequence (SEQ ID NO:2) corresponding to the cDNA encoding N38 (SEQ ID NO:1) obtained in Example 1. The first residue, Met corresponding to initiation codon ATG was removed by processing during its production;

FIG. 4 shows an amino acid sequence (SEQ ID NO:4) of N63 obtained in Example 2;

Figure 3:
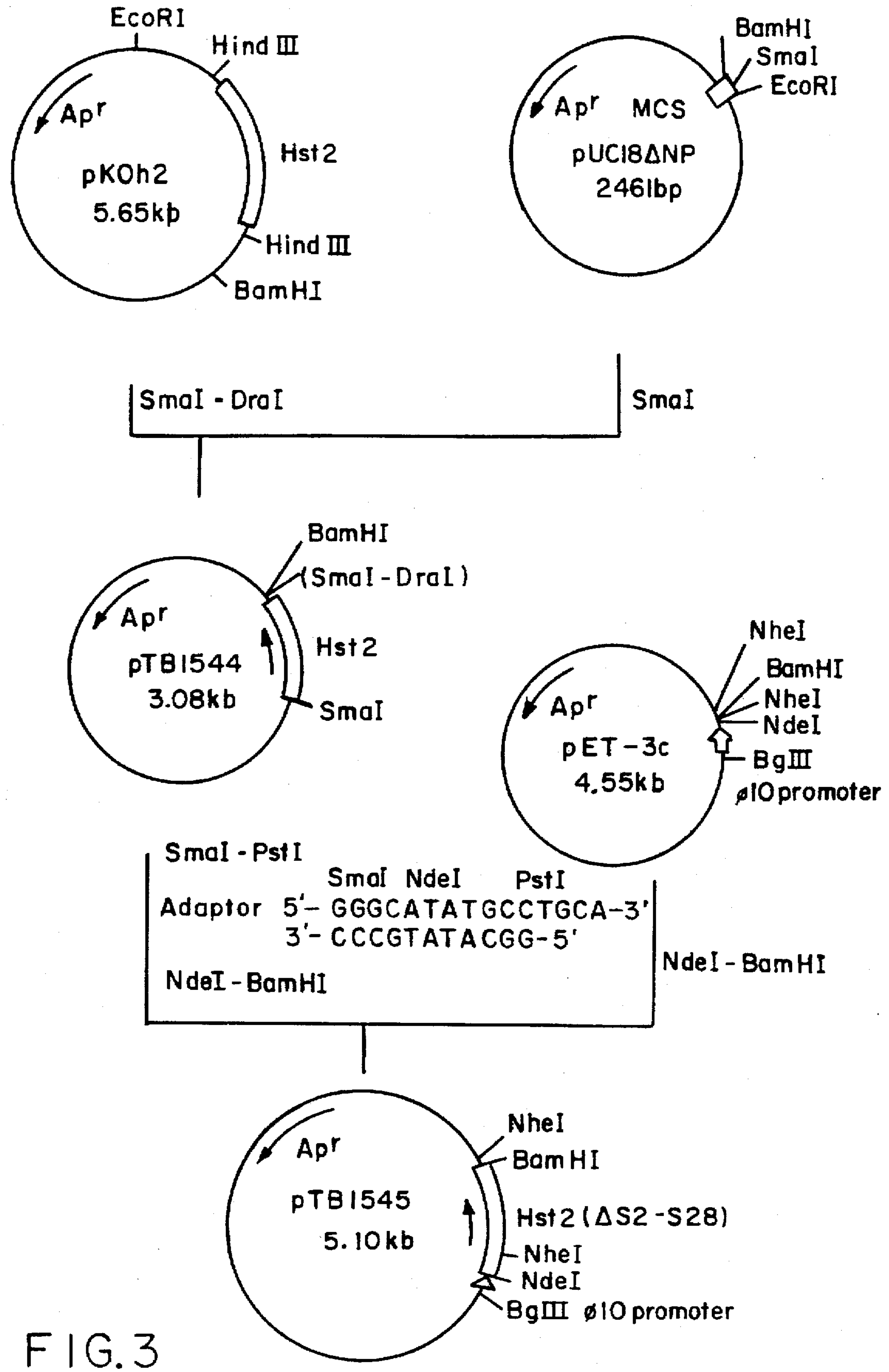
FIG. 3 is a schematic representation showing the construction of plasmid pTB1545 obtained in Example 1.

PREFERRED EMBODIMENT OF THE INVENTION hst-2 is a protein having an amino acid sequence comprising 208 amino acids (SEQ ID NO: 6) as a whole molecule, taking Met corresponding to the N-terminal initiation codon shown in FIG. 1 as amino acid residue No. 1. In this specification, the constituent amino acids of hst-2 are indicated by the numbers of amino acid residues in accordance with those of this sequence (European Patent Application No. 488196) (SEQ ID NO: 6). Further, the "hst-2 polypeptide" in the present specification is a general term for polypeptides having hst-2 activity. The polypeptides include the polypeptide of SEQ ID NO:6 and a fragment thereof.

The polypeptides (I) of the present invention include a derivative in which the fragment of the sequence represented by X has at least one amino acid from the C-terminus of its amino acid sequence and which has hst-2 activity. The fragment includes the C-terminus amino acid residue Gly. Among them, it is preferred that 1 to 25 successive amino acids are deleted from the N-terminus of the amino acid sequence.

However, they may be deleted in a central portion or on the carboxyl-terminal side of the amino acid sequence represented by X as long as the polypeptide has hst-2 activity.

On the other hand, the polypeptide having hst-2 activity (hst-2 polypeptide) used in the method for promoting an increase in number of platelets may be any deletion muteins, espeicially 38 to 63 amino acid residue deletion muteins are preferable.

The chemical structure of the hst-2 polypeptides include polypeptide (I) of the present invention varies depending on various factors such as operations and reagents in production and purification stages. For example, the hst-2 polypeptides of the present invention are sometimes obtained as salts such as salts of inorganic acids (for example, hydrochlorides and phosphates), salts of organic acids (for example, acetates and trifluoroacetates) and salts of bases (for example, alkaline metal salts such as sodium salts and potassium salts, alkaline earth metal salts such as calcium salts and magnesium metals, and ammonium salts). The hst-2 polypeptides of the present invention include these salts. Further, the hst-2 polypeptides of the present invention may be derivatives to which sugar chains, lipids, acetyl groups, etc. are added. Thus, the polypeptides of the present invention may be the salts or the derivatives as described above. The hst-2 polypeptides of the present invention include any type of polypeptides as long as they have hst-2 activity or they are easily converted to the active type in vivo.

The biological activity of the hst-2 polypeptides of the present invention can be assayed, for example, by measuring the stimulation of DNA synthesis of mouse BALB/c3T3 cells based upon the uptake of tritium thymidine ($[^3H]$ thymidine) in accordance with the method of Sasada et al. [*Mol. Cell Biol.*, 8, 588–594 (1988)], measuring the growth promotion of the vascular endothelial cells in accordance with the method of Tada et al. [*Journal of Immunological Methods*, 93, 157 (1986)], or measuring the angiogenesis on the arian embryo allantois in accordance with the method of Auerbach [*Developmental Biology*, 41, 391 (1974)].

The expression vector containing the DNA having the nucleotide sequence coding for the hst-2 polypeptides of the present invention can be prepared, for example, by the following process:

(i) RNA coding for an hst-2 protein is isolated;

(ii) Single stranded complementary DNA (cDNA) is synthesized against the RNA, followed by synthesis of double stranded DNA;

(iii) The complementary DNA is introduced into a plasmid;

(iv) A host cell is transformed with the recombinant plasmid thus obtained;

(v) After cultivation of the transformant thus obtained, the plasmid containing the desired DNA is isolated from the transformant by an appropriate method such as colony hybridization using a DNA probe;

(vi) The desired cloned DNA is cut out from the plasmid;

(vii) Deletion fitting the purpose is conducted on the cloned DNA;

(viii) An oligonucleotide containing an ATG codon is bound thereto in some cases; and (ix) The resulting DNA is ligated downstream from a promoter in a vehicle.

The above-mentioned RNA coding for hst-2 can be obtained from the muscles or the testes (de Lapeyriere et al., shown above) in which the hst-2 protein is possibly localized, the leukemia cell strain HEL (Martin and Papayannoponlou, shown above) in which the peptide is considered to be produced, or NIH3T3 transformants with human hst-2 genes [European Patent Publication No. 488196 or Iida et al., *Oncogene*, 7, 303 (1992)].

Methods for preparing the RNA from the human organs and cells include the guanidine thiocyanate method [J. M. Chirgwin et al., *Biochemistry*, 18, 5294 (1979)].

Using the RNA thus obtained as a template, cDNA is synthesized. The cDNA is introduced, for example, into λ phage vector λgt10 [T. V. Huynh et al. *DNA Cloning A Practical Approach*, p.79, IRL Press Oxford (1985)], for example, in accordance with the method of Watson and Jackson [C. J. Watson and J. F. Jackson, *DNA Cloning, A Practical Approach*, p.49, IRL Press Oxford (1985)], and *Escherichia coli* such as C600 and Hf1A [T. V. Huynh et al., ibid.] is infected therewith, whereby a cDNA library can be produced.

Desired clones are selected from the cDNA library thus obtained by known methods such as the plaque hybridization method [T. Maniatis et al., *Molecular Cloning*, p.320, Cold Spring Harbor Laboratory (1982)] and the DNA nucleotide sequence determination method [*Proc. Natl. Acad. Sci. U.S.A.*, 74, 560 (1977) and *Nucl. Acids Res.*, 9, 309 (1981)].

Then, the phage clones are collected, and phage DNA is extracted, for example, by the method of Davis et al. [Davis et al., *Advanced Bacterial Genetics*, Cold Spring Harbor Laboratory (1980)]. A cDNA portion thereof is cut out with a restriction enzyme, and introduced into a plasmid such as pUC13 for convenient use.

The plasmid having the DNA containing the nucleotide sequence coding for the above-mentioned cloned hst-2 can be used as it is or after digestion with a restriction enzyme if desired.

The cloned gene can be ligated downstream from a promoter in a vehicle (vector) suitable for expression, thereby obtaining an expression vector.

In order to produce the hst-2 polypeptides including the polypeptide (I) of the present invention, site-directed mutagenesis can be employed, in addition to other conventional recombinant DNA techniques. Site-directed mutagenesis is well known and described in R. F. Lather and J. P. Lecog, *Genetic Engineering*, p.31–50, Academic Press (1983). Mutagenesis directed to an oligonucleotide is described in M. Smith and S. Gillam, *Genetic Engineering: Principles and Methods*, vol. 3, p.1–32, Plenum Press (1981).

In order to produce a structural gene coding for the polypeptide (I) of the present invention, for example, (a) single stranded DNA comprising a single strand of a structural gene of hst-2 is hybridized with a mutant oligonucleotide primer, (b) the primer is extended with DNA polymerase to form a mutational heteroduplex, and (c) the mutational heteroduplex is duplicated.

The size of the oligonucleotide primer is determined according to the conditions necessary for stable hybridization of the primer to a gene region in which the mutation is introduced, or the limitation of the oligonucleotide synthesis methods available at present. Factors (the whole size and the size of a portion by-passing a mutation site) to be considered in designing an oligonucleotide used in mutagenesis directed to the oligonucleotide are described by M. Smith and S. Gillam, supra. In general, the entire length of the nucleotide is such as to optimize stable, unique hybridization at the mutation site, and the extensions from the mutation site to 5'- and 3'-terminal ends shall be a size sufficient to avoid edition of mutation by exonuclease activity of DNA polymerase. The oligonucleotide used for mutagenesis according to the present invention usually contains about 12 to about 24 nucleotides, preferably about 14 to about 20 nucleotides, and more preferably about 14 to about 18 nucleotides. Usually, these contain at least about 3 nucleotides on the 3'-terminal side of a mutation site.

When it is intended to obtain a hst-2 polypeptide in which at least one hst-2-constituent amino acid is deleted, three methods for producing a mutagenized hst-2 gene are considered according to the portion at which the constituent amino acid is deleted. The first is by a deletion from the amino terminus of hst-2, the second is by a deletion from the central portion of hst-2, and the third is by a deletion from the carboxyl terminus of hst-2.

When the amino terminus is deleted, a codon of a gene coding for the carboxyl terminus of an amino acid sequence to be deleted is mutagenized to initiation codon ATG coding for Met by the use of site-directed mutagenesis, and a recognition site for an appropriate restriction enzyme is formed on the 5'-terminal side of the codon for easy ligation with a promoter, or the ATG of the oligonucleotide is adjusted to an appropriate reading frame to ligate the oligonucleotide with the gene the amino terminus of which is deleted with a restriction enzyme. According to these methods, the mutagenized gene for the polypeptide (I) of the present invention is prepared by mutagenizing a codon of a gene coding for a residue of the 38th Ser to 63rd Ala of SEQ ID NO:6.

When the central portion of the amino acid sequence is deleted, recognition sites for a unique restriction enzyme can be formed on the 5'- and 3'-terminal sides of a gene coding for the amino acid sequence to be deleted, using site-directed mutagenesis, and these sites are digested with an enzyme to remove the portion coding for the sequence. Ligation of both the resulting fragments provides a gene coding the hst-2 in which the desired amino acid(s) is deleted. Needless to say, deviation of a reading frame caused by digestion with the restriction enzyme should be avoided.

When the amino acid sequence on the carboxyl terminal side is deleted, a codon of a gene coding for the amino acid(s) on the amino terminal side in the amino acid sequence to be deleted is mutagenized to a stop codon by site-directed mutagenesis.

Although the hst-2 polypeptides including the polypeptide (I) of the present invention lacks the constituent amino acids of hst-2 as described above, at least one amino acid of these constituent amino acids may be further substituted by another amino acid, as long as the mutein has hst-2 activity.

Examples of the constituent amino acids before substitution (amino acids to be substituted) include any amino acids of cysteine and amino acids other than cysteine (for example, aspartic acid and arginine).

When the amino acid to be substituted is cysteine, for example, neutral amino acids are preferred as amino acids substituted therefor (substituting amino acids). Examples of the neutral amino acids include glycine, valine, alanine, leucine, isoleucine, tyrosine, phenylalanine, histidine, tryptophan, serine, threonine and methionine. In particular, serine and threonine are preferred.

When the amino acid to be substituted is any one other than cysteine, amino acids which are different, for example, in hydrophilicity, hydrophobicity or electric charge from the amino acid to be substituted are selected as the substituting amino acids. Specifically, when the amino acid to be substituted is aspartic acid, the substituting amino acids include asparagine, threonine, valine, phenylalanine and arginine. In particular, asparagine and arginine are preferred.

When the amino acid to be substituted is arginine, the substituting amino acids include glutamine, threonine, leucine, phenylalanine and aspartic acid. In particular, glutamine is preferred.

When the hst-2 polypeptides including polypeptide (I) of the present invention are produced by site-directed mutagenesis, a plurality of mutations may be introduced in the DNA sequence. Namely, any codons may be selected as long as they are DNA codons corresponding to the amino acids.

For example, when the constituent amino acid is an amino acid other than cysteine, which is substituted by another amino acid to obtain a mutein, a mutagenized hst-2 gene is produced by a method in which a codon is mutagenized with an oligonucleotide primer in the same manner as with cysteine. However, the design of the oligonucleotide primer varies, of course, depending on what amino acid is mutagenized.

The primer is hybridized to a single-stranded phage such as M13 in which a single strand of an hst-2 gene is cloned [Yanisch-Perror, C. Vieira and J. Messing, *Gene*, 33, (103–119) (1985) and J. Messing, *Methods in Enzymology*, 101, 20–78 (1983)], fd [R. Herrman et al., *Mol. Gen. Genet.*, 177, 231 (1980)] or φX174 [M. Smith and S. Gillam, *Genetic Engineering*, vol. 3, p.1–32, Plenum Press (1981)]. The phage can transfer both sense and anti-sense chains of the gene. When the phage transfers the anti-sense chain, the primer may not be the same as with a region of the sense chain because of degeneracy of the codon, in addition to a codon to be mutagenized. Similarly, when the phage transfers the sense chain, the primer may not be complementary to the region of the sense chain, in addition to a codon to be mutagenized forming pairing with the codon to be deleted. Conditions used for hybridization are described by M. Smith and S. Gillam, supra. The temperature usually ranges from about 0° to about 70° C., and more generally from about 10° to about 50° C. After hybridization, the primer is extended on phage DNA by reaction with *E. coli* DNA polymerase I, T4 DNA polymerase, reverse transcriptase or another appropriate DNA polymerase. The resulting ds DNA is converted to closed-ring ds DNA by treatment with a DNA ligase such as T4 DNA ligase. A DNA molecule containing a single-stranded region can be disrupted by S1 endonuclease treatment.

The resulting mutagenized heteroduplex is used to transform competent host organisms and cells. Duplication of the heteroduplex with the hosts produces progeny from both chains. Following the duplication, mutant genes are isolated from progeny of mutant chains and inserted into appropriate vectors, which are used for transformation of appropriate host organisms and cells.

Then, phage DNA transferring mutagenized genes is isolated and introduced into a plasmid.

The plasmids into which the DNA is introduced include, for example, plasmids pBR322 [*Gene,* 2, 95 (1977)], pBR325 [*Gene,* 4, 121 (1978)], pUC12 [*Gene,* 19, 259 (1982)] and pUC13 [*Gene,* 19, 259 (1982)], which are derived from *E. coli*; and plasmid pUB110 [*Biochemical and Biophysical Research Communication,* 112, 6678 (1983)] which is derived from *Bacillus subtilis.* However, any other plasmid can be used as long as it is replicable and retainable in the host.

Methods for introducing the DNA into the plasmid include, for example, the method described in T. Maniatis et al., *Molecular Cloning,* p.239, Cold Spring Harbor Laboratory (1982).

The cloned gene is ligated downstream from a promoter in a vehicle (vector) suitable for expression, whereby an expression vector can be obtained.

Examples of the vehicles (vectors) for preparing recombinant vectors include plasmids pBR322 (shown above), pBR325 (shown above), pUC12 (shown above) and pUC13 (shown above), which are derived from *E. coli*; and plasmids pUB110, pTP5 and pC194, which are derived from *Bacillus subtilis*, yeast-derived plasmids (for example, pSH19 and pSH15), bacteriophages such as λ phage, and animal viruses such as retroviruses and vaccinia viruses.

The gene may have ATG as a translation initiation codon at the 5'-terminus thereof, and TAA, TGA or TAG as a translation termination codon at the 3'-terminus thereof. A promoter is further ligated upstream therefrom and operably linked thereto to express the gene. The promoter used in this invention may be any as long as it is suitable for expression in a host selected for the gene expression.

For example, when the host used for transformation is Escherichia, it is preferred to use a trp promoter, a lac promoter, a rec A promoter, a λpL promoter, a lpp promoter, a T7 promoter, etc. When the host is Bacillus, it is preferred to use an SPO1 promoter, an SPO2 promoter, penP promoter, etc. When the host is yeast, it is preferred to use a PHO5 promoter, a PGK promoter, a GAP promoter, an ADH promoter, etc. It is preferred that the host is Escherichia, and that the promoter is the trp promoter or the T7 promoter, among others.

When the host is an animal cell, a SV40-derived promoter, a retrovirus promoter, etc. can be used. The SV40-derived promoter is particularly preferable.

By using the DNA-containing vector thus constructed, the transformant is prepared.

The host cells that can be used include Escherichia, Bacillus, yeast and animal cells.

Examples of Escherichia described above include *E. coli* K12DHI [*Proc. Natl. Acad. Sci. U.S.A.,* 60, 160 (1968)], M103 [*Nucl. Acids Res.,* 9, 309 (1981)], JA221 [*J. Mol. Biol.,* 120, 517, (1978)], HB101 [*J. Mol. Biol.,* 41, 459 (1969)] and C600 [*Genetics,* 39, 440 (1954)].

Examples of Bacillus described above include *Bacillus subtilis* MI114 [*Gene,* 24, 255 (1983)] and 207–21 [*J. Biochem.,* 95, 87 (1984)].

Examples of the yeast described above include *Saccharomyces cereviciae* AH22R⁻, NA87-11A and DKD-5D.

Examples of the animal cells, cell lines preferably used include monkey cell COS-7 [*Cell,* 23, 157 (1981)], vero, Chinese hamster cell CHO, mouse L cell and human FL cell.

The transformation of Escherichia described above is carried out, for example, according to the method described in *Proc. Natl. Acad. Sci. U.S.A.,* 69, 2110 (1972) and *Gene,* 17, 107 (1982).

The transformation of Bacillus is carried out, for example, according to the method described in *Molecular & General Genetics,* 168, 111 (1979).

The transformation of the yeast is carried out, for example, according to the method described in *Proc. Natl. Acad. Sci. U.S.A.,* 75, 1929 (1978).

The transformation of the animal cells is carried out, for example, according to the method described in *Virology,* 52, 456 (1973).

Thus, the transformants are obtained by transforming with the vectors containing the desired hst-2 polypeptide such as polypeptide (I).

When bacterial transformants are cultivated, a liquid medium is appropriate as a medium used for cultivation. Carbon sources, nitrogen sources, inorganic compounds and others necessary for growth of the transformants are contained therein. Examples of the carbon sources include glucose, dextrin, soluble starch and sucrose. Examples of the nitrogen sources include inorganic or organic materials such as ammonium salts, nitrates, corn steep liquor, peptone, casein, meat extracts, soybean meal and potato extract solution. The inorganic compounds include, for example, calcium chloride, sodium dihydrogenphosphate and magnesium chloride. Yeast extracts, vitamins, growth promoting factors and the like may be further added thereto.

The pH of the medium is preferably about 6 to about 8.

As the medium used for cultivation of Escherichia, for example, M9 medium containing glucose and Casamino Acids [Miller, *Journal of Experiments in Molecular Genetics,* 431–433, Cold Spring Harbor Laboratory, New York (1972)] is preferably used. In order to make the promoter act efficiently, a drug such as 3β-indolylacrylic acid may be added thereto if necessary.

When the Escherichia transformants are cultivated, the cultivation is usually carried out at about 15° to about 43° C. for about 3 to about 24 hours with aeration or agitation if necessary.

When the Bacillus transformants are cultivated, the cultivation is usually carried out at about 30° to about 40° C. for about 6 to about 24 hours with aeration or agitation if necessary.

When the yeast transformants are cultivated, examples of the media include Burkholder minimum medium [K. L. Bostian, *Proc. Natl. Acad. Sci. U.S.A.,* 77, 4505 (1980)]. The pH of the medium is preferably adjusted to about 5 to about 8. The cultivation is usually carried out at about 20° to about 35° C. for about 24 to about 72 hours with aeration or agitation if necessary.

When the animal cell transformants are cultivated, examples of the media include MEM medium [*Science,* 122, 501 (1952)], DMEM medium [*Virology*, 8, 396 (1959)], RPMI1640 medium [*J. Am. Med. Assoc.*, 199, 519 (1967)] and 199 medium [*Proc. Soc. Biol. Med.*, 73, 1 (1950)]. About 5 to about 20% fetal calf serum may be further added thereto. The pH is preferably about 6 to about 8. The cultivation is usually carried out at about 30° to about 40° C. for about 15 to about 60 hours, with aeration or agitation if necessary.

The hst-2 polypeptides including the polypeptide (I) formed and accumulated in the above-mentioned culture products, namely in cells or outside cells, can be isolated and purified, for example, by the following method.

When hst-2 polypeptides including the polypeptide (I) are extracted from the cultivated cells, the cells are collected by methods known in the art after cultivation. Then, the collected cells are suspended in buffer solutions containing protein denaturants such as guanidine hydrochloride to elute the desired proteins out of the cells. The cells can also be disrupted by a French press, ultrasonic treatment, an enzyme such as lysozyme and/or freeze-thawing, followed by centrifugation to obtain the hst-2 polypeptides including polypeptide (I). A combination of the enzyme such as lysozyme and ultrasonic treatment is preferably used among others.

For example, the polypeptide (I) of the present invention can be purified from a supernatant by appropriate combinations of known separating and purifying methods. These known separating and purifying methods include methods utilizing solubility such as salt precipitation and solvent precipitation, methods mainly utilizing a difference in molecular weight such as dialysis, ultrafiltration, gel filtration and SDS-polyacrylamide gel electrophoresis, methods utilizing a difference in electric charge such as ion-exchange chromatography, methods utilizing specific affinity such as affinity chromatography, methods utilizing a difference in hydrophobicity such as reverse phase high performance liquid chromatography, and methods utilizing a difference in isoelectric point such as isoelectro-focussing electrophoresis.

More specifically, the above-mentioned supernatant can be subjected to ion-exchange chromatography using DEAE cellulose, thereby being able to remove contaminants such as nucleic acids and acidic proteins. For example, it is effective to subject the supernatant to a DEAE cellulose column equilibrated with a buffer such as Tris around neutrality and collect fractions not adsorbed to the column. Further, the polypeptide (I) can be purified by subjecting the supernatant to ion-exchange chromatography using carboxymethyl (CM) cellulose as a carrier to allow the polypeptide to be adsorbed by the carrier and eluting the polypeptide (I) by use of a salt solution.

The polypeptide (I) can be directly purified from cell extracts by column chromatography using acidic resins such as CM Sephadex. For example, the supernatant is subjected to a CM-Sephadex column equilibrated with a weakly acidic buffer (for example, phosphate buffer), which causes efficient purification. After washing the column with the same buffer, the column is eluted with a buffer further containing a salt (for example, NaCl), thereby allowing the polypeptide (I) to be eluted. These eluates can be lyophilized after dialysis.

Affinity chromatography using heparin-Sepharose as a carrier can conveniently be applied to the deletion type muteins of hst-2 in *E. coli* extract for purification of the polypeptide (I). For example, the above-mentioned eluate is loaded onto a heparin-Sepharose column equilibrated with a buffer solution around neutrality such as Tris buffer or phosphate buffer. After thorough washing, the column is eluted with a linear gradient of NaCl, thereby permitting the polypeptide (I) to be purified.

In particular, heparin columns developed for high performance liquid chromatography (HPLC) (for example, Shodex AF-pak HR-894, Showa Denko) are effective.

As with the above-mentioned heparin-Sepharose column, the eluate is loaded onto the heparin column equilibrated with a buffer solution around neutrality. After thorough washing, the column is eluted with a linear gradient of NaCl. Repeated cycles of this column step can be used for obtaining a highly purified sample. Thus, the polypeptide (I) of the present invention can be recovered as a highly purified sample.

The sample thus obtained can also be dialyzed and lyophilized to yield a dry powder. Further, it is preferred that serum albumin is added to the sample as a carrier for storage, because the sample can be prevented from being adsorbed by a container.

The coexistence of a slight amount of a reducing agent in the purification course or the storage course is suitable for preventing the oxidation of the sample. The reducing agents include β-mercaptoethanol, dithiothreitol and glutathione.

Thus, the polypeptides (I) of the present invention are obtained which are substantially pure and substantially free from a pyrogen and an endotoxin. The substantially pure polypeptide (I) of the present invention contains the polypeptide (I) in an amount of 95% (w/w) or more as a protein content, and more preferably in an amount of 98% (w/w) or more. The substantially pyrogen and endotoxin free product reacts negatively in the limulus lysate test.

The hst-2 activity of the polypeptide thus formed can be assayed by growth promoting effect of known BALB/c3T3 cells.

According to the cells transfected or transformed with the DNA of the present invention, the polypeptide (I) can be produced in large amounts also in various cells in which the hst-2 polypeptides are essentially synthesized only in small amounts, or not synthesized at all, which causes advantageous derivation of the polypeptide (I) of the present invention.

The expression plasmids containing the genes coding for the polypeptides (I) of the present invention can produce the polypeptides in large amounts in various cells by introducing the plasmids into the cells. The polypeptide (I) can therefore be obtained in large amounts.

The polypeptide (I) produced herein has the activity of promoting the growth of cells such as vascular endothelial cells and angiogenesis promoting activity, and are low in toxicity, so that they can be used as therapeutic agents such as drugs for promoting treatment of burns, wounds and postoperative tissues. In addition, they can be used as reagents for promoting cell cultivation.

When the polypeptide (I) of the present invention is used as the drugs, it can be safely given parenterally or orally to warm-blooded animals (such as humans, mice, rats, hamsters, rabbits, dogs and cats), in a powder form as are or as pharmaceutical compositions (such as injections, tablets, capsules, solutions and ointments) with pharmaceutically acceptable carriers, excipients and diluents.

The injections are prepared by conventional methods using, for example, physiological saline or aqueous solutions containing glucose or other auxiliary agents. The pharmaceutical compositions such as tablets and capsules can also be prepared in accordance with conventional methods. When the injections, the solutions, the tablets and the capsules are prepared as the pharmaceutical compositions, they are prepared under aseptic conditions.

When the polypeptide (I) of the present invention is used as the drug described above, it is given, for example, to the above-mentioned warm-blooded animals in an appropriate amount ranging from about 1 ng to about 100 μg/kg daily, taking into account the routes of administration, symptoms, etc. The hst-2 polypeptides are also used in an appropriate amount selected from the same range of amount in the present method.

Further, when the polypeptides of the present invention are used as the reagents for promoting cell cultivation, they are added to media preferably in an amount of about 0.01 to about 10 μg per liter of medium, and more preferably in an amount of about 0.1 to about 10 μg per liter of medium. Furthermore, when the polypeptide (I) is used as the reagent for promoting cultivation of megakaryocyte precursor cells, they are added to media preferably in an amount of about 0.1 to about 10 mg per liter of medium, and more preferably in an amount of about 0.5 to about 10 mg per liter of medium.

The polypeptide (I) of the present invention exhibits excellent cell growth promoting activity and are stable under acidic conditions, so that they can also be used as therapeutic agents for ulcers such as gastrointestinal ulcers and for promoting treatment of burns, wounds, etc. Further, they exhibit megakaryocyte growth promoting activity. They can be therefore applied to improve thrombocytopenic symptoms congenital or as side effects of chemotherapeutics.

The therapeutic composition of the present invention can be use as the platelet-increasing agent. Administration of the platelet-increasing agents of the present invention can increase the number of platelets in the peripheral blood. In chemotherapy of cancers, administration of almost all chemotherapeutics induces a decrease in the number of platelets, which hinders administering the chemotherapeutics in sufficient amounts. The same is true for radiotherapy. A decrease in the number of platelets is observed at about 3 to about 15 days after administration of the chemotherapeutics. The platelet-increasing agents of the present invention can be given immediately after administration of the chemotherapeutics, or after observation of a decrease in the number of platelets to restore the number of platelets. Furthermore, they can also be administered to previously increase the number of platelets by giving the platelet-increasing agents of the present invention before administration of the chemotherapeutics.

The therapeutic composition of the present invention can increase platelets in number to restore the number of platelets decreased by chemotherapy, thereby enhancing the effect of treatment and restoring patients from serious symptoms.

Thus, platelet-increasing agents of the present invention can be used as anticancer aids as long as the cancer growth is not promoted.

Examples of anticancer agents used as the chemotherapeutics include alkylating agents (for example, nitrogen mustard N-oxide, cyclophosphamide, melphalan, carboquone, busulfan, nimustine hydrochloride, ranimustine and dacarbazine), antimetabolites (for example, fluorouracil, tegaful, cytarabine, ancitabine hydrochloride, broxuridine, doxifluridine, mercaptopurine, thioinosine and methotrexate), antibiotics (for example, mitomycin, bleomycin, daunorubicin hydrochloride, doxorubicin hydrochloride, pirarubicin hydrochloride, aclarubicin hydrochloride, neocarzinostatin and actinomycin D), plant alkaloids (for example, vincristine sulfate, vindesine sulfate, vinblastine sulfate and etoposide), hormone agents (for example, tamoxifen citrate), platinum coordination component (for example, carboplatin, cisplatin) and others (for example, procarbazine hydrochloride, mitobronitol and mitoxanton hydrochloride).

The polypeptide (I) of the present invention can be obtained in large amounts and in high purity by introduction of the gene into various cells.

When nucleotides, amino acids and so on are indicated by abbreviations in the specification and drawings, the abbreviations adopted by the IUPAC-IUB Commission on Biochemical Nomenclature or commonly used in the art are employed. For example, the following abbreviations are used. When the amino acids are capable of existing as optical isomers, it is understood that the L-forms are represented unless otherwise specified.

DNA: Deoxyribonucleic acid
cDNA: Complementary deoxyribonucleic acid
A: Adenine
T: Thymine
G: Guanine
C: Cytosine
RNA: Ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
Tdr: Thymidine
EDTA: Ethylenediaminetetraacetic acid
SDS: Sodium dodecyl sulfate
Gly: Glycine
Ala: Alanine
Val: Valine
Leu: Leucine
Ile: Isoleucine
Ser: Serine
Thr: Threonine
Cys: Cysteine
Met: Methionine
Glu: Glutamic acid
Asp: Aspartic acid
Lys: Lysine
Arg: Arginine
His: Histidine
Phe: Phenylalanine
Tyr: Tyrosine
Trp: Tryptophan
Pro: Proline
Asn: Asparagine
Gln: Glutamine

EXAMPLES

The transformants obtained in the following Examples were deposited with the Institute for Fermentation, Osaka, Japan (IFO) and with the National Institute of Bioscience and Human-technology (NIBH) (Formerly the Fermentation Research Institute), the Agency of Industrial Science and Technology, the Ministry of International Trade and Industry, Japan. The accession numbers and the deposit dates are shown in Table 1.

TABLE 1

| Transformant | IFO | FRI |
|---|---|---|
| *E. coli* MM294(DE3)/ pLysS · pTB1545 (Example 1-b)) | IFO 15430 (Jan. 19, 1993) | FERM BP-4179 Feb. 8., 1993) |
| *E. coli* MM294(DE3)/ pLysS · pTB1547 | IFO 15431 (Jan. 19, 1993) | FERM BP-4180 (Feb. 8, 1993) |

The present invention will be described in more detail with the following Examples. It is understood of course that they are not intended to limit the scope of the invention.

The polypeptide obtained in Example 1 in which amino acids from the N-terminus to amino acid residue No. 38 of SEQ ID NO:6 are deleted is called N38, and its amino acid sequence is shown in FIG. 2 (SEQ ID NO:1).

The mutein obtained in Example 2 in which amino acids from the N-terminus to amino acid residue No. 63 of hst-2 are deleted is called N63, and its amino acid sequence is shown in FIG. 4 (SEQ ID NO:3).

Example 1

Expression of N38 a) Construction of an Expression Plasmid

Plasmid pKOh2 containing human hst-2 cDNA [*Oncogene,* 7, 303–309 (1992)] was cleaved with SmaI-DraI to obtain a 0.62-kb DNA fragment. This fragment was inserted into the SmaI site of the NdeI-PstI deletion vector of pUC18 to obtain plasmid pTB1544 with the BamHI site arranged behind the DraI site. Synthetic oligonucleotides 5'GGGCATATGCCTGCA3' (SEQ ID NO:9) and 5'GGCATATGCCC3' (SEQ ID NO:10) were inserted into the SmaI-PstI sites, followed by digestion with NdeI-BamHI to obtain an NdeI-BamHI fragment. The above-mentioned fragment (containing a gene in which initiation codon ATG is attached before CCT coding for the 39th Pro) was inserted between NdeI-BamHI of expression vector pET-3c for *E. coli* having a $\phi$10 promoter of T7 phage [*Gene,* 56, 125–135 (1987)] to obtain pTB1545 (FIG. 3).

b) Expression of the cDNA in *E. coli*

An RNA polymerase gene of T7 phage was introduced into a strain of *E. coli* MM294 to obtain $\lambda$ phage DE3 [F. W. Studiert et al., *J. Mol. Biol.,* 189, 113–130 (1986)], which was lysogenized. Plasmid pLysS having a lysozyme gene of T7 phage [F. W. Studier et al., ibid.] was further introduced thereinto to prepare a strain of *E. coli* MM294(DE3)/pLysS.

The plasmid pTB1545 obtained in (a) described above was introduced into the *E. coli* MM294(DE3)/pLysS strain to prepare *E. coli* MM294(DE3)/pLysS.pTB1545 (IFO 15430, FERM BP-4179). The resulting cells were cultivated in L medium containing 10 μg/ml chloramphenicol and 100 μg/ml ampicillin, and isopropyl β-D-thiogalactopyranoside (IPTG) was added to give a final concentration of 0.1 mM at the time when the Klett value reached about 180. Then, cultivation was further continued for 4 hours. The cells were collected by centrifugation and washed with phosphate buffered saline (PBS) cooled with ice. Then, the cells were recollected and stored at −20° C. until they are to be used.

Example 2

Expression of N63 a) Construction of an Expression Plasmid

Figure 5:
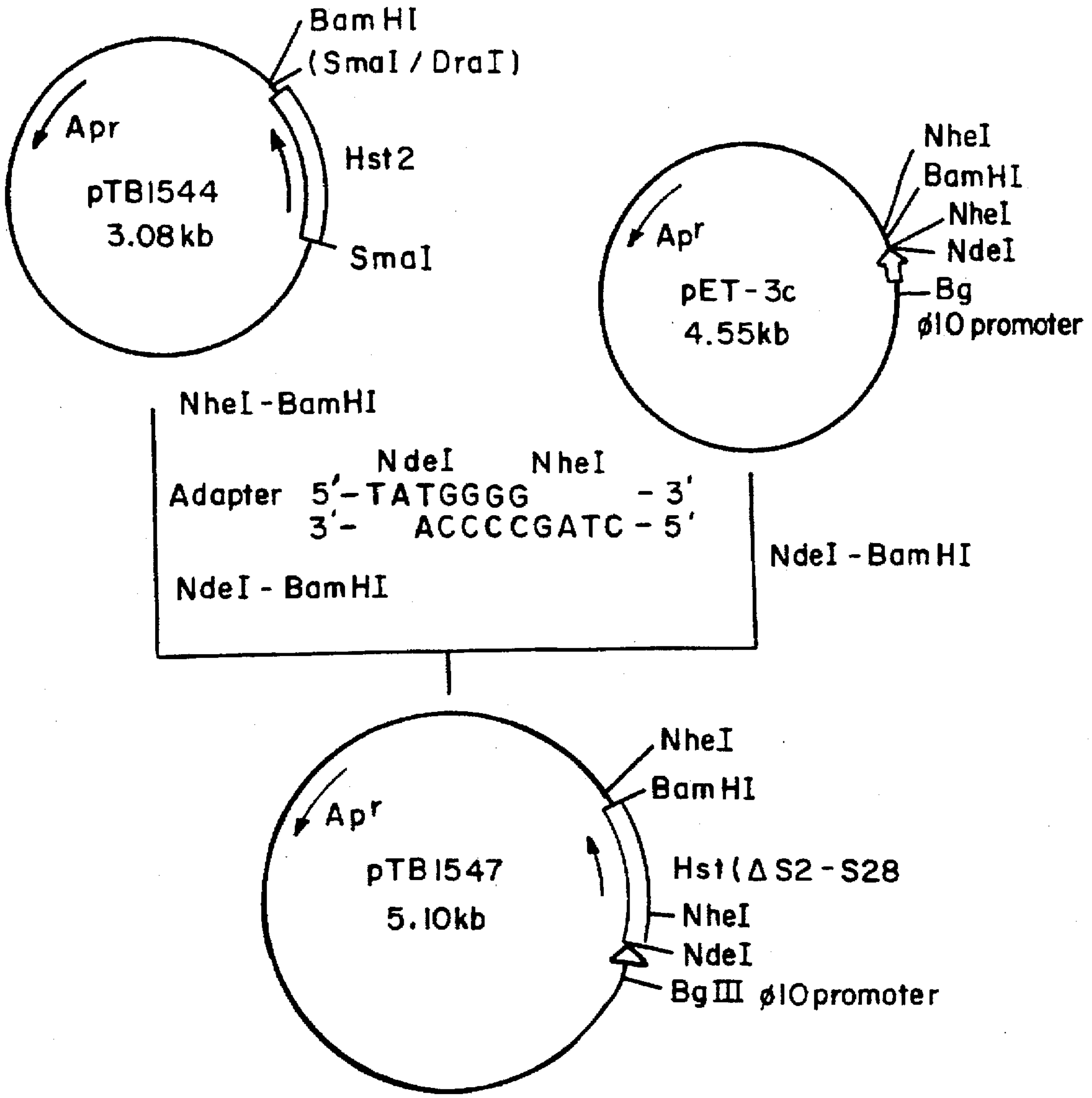
FIG. 5 is a schematic representation showing the construction of plasmid pTB1547 obtained in Example 2.

Plasmid pTB1544 obtained in Example 1-a) was cleaved with NheI-BamHI to obtain a 0.46-kb DNA fragment. This fragment and synthetic oligonucleotides 5'TATGGGG3' and 5'CTAGCCCCA3' were ligated with the 5'-terminal side of the above-mentioned 0.46-kb DNA fragment to obtain a 0.47-kb NdeI-BamHI DNA fragment (containing a gene in which initiation codon ATG is attached before CCT coding for the 64th Gly). This fragment was inserted between NdeI-BamHI of expression vector pET-3c for *E. coli* having a $\phi$10 promoter of T7 phage (shown above) to obtain pTB1547 (FIG. 5).

b) Expression of the cDNA in *E. coli*

The plasmid pTB1547 obtained in (a) described above was introduced into the *E. coli* MM294(DE3)/pLysS strain prepared in Example 1-b) to prepare *E. coli* MM294(DE3) /pLysS.pTB1548 (IFO 15431, FERM BP-4180). The resulting cells were cultivated in L medium containing 10 μg/ml chloramphenicol and 100 μg/ml ampicillin, and IPTG was added to give a final concentration of 0.1 mM at the time when the Klett value reached about 180. Then, cultivation was further continued for 4 hours. The cells were collected by centrifugation and washed with PBS cooled with ice. Then, the cells were recollected and stored at −20° C. until they are to be used.

Example 3

Purification of Recombinant N38 a) Extraction and a Heparin Column

The cells described in Example 1 collected from the 1-liter culture were suspended in 25 ml of 10 mM Tris-HCl (pH 7.4), 10 mM EDTA, 0.5M NaCl, 10% sucrose and 1 mM PMSF cooled with ice, and egg white lysozyme was added thereto to yield a concentration of 0.5 mg/ml. After standing in ice for 1 hour, the suspension was incubated at 37° C. for 5 minutes, and subjected to ultrasonic treatment (for 20 seconds, twice) and centrifugation (SORVALL, at 18 krpm at 4° C. for 30 minutes) to obtain a supernatant as a cell extract.

25 ml of the cell extract was loaded onto a Q Sepharose (Pharmacia) column (5 cm in diameter×5 cm) equilibrated with a solution of 20 mMTris-HCl (pH 7.6) and 0.5M NaCl, thereby removing nucleic acid components in the extract. A solution flowing through the column (fractions not adsorbed to the Q Sepharose column: 45 ml) was combined with column washings of the solution of 20 mM Tris-HCl (pH 7.6) and 0.5M NaCl. This fraction was subjected to a high performance liquid chromatography apparatus (Gilson) equipped with a heparin column, Shodex AF-paK AHR-894 (8 mm ID×25 cm, Showa Denko). The column was washed with a solution of 20 mM Tris-HCl (pH 7.6), and then with a solution of 20 mM Tris-HCl (pH 7.6) and 0.7M NaCl. Thereafter, the column was eluted with a linear gradient of 0.7 to 2M NaCl in 20 mM Tris-HCl buffer (pH 7.6) at a flow rate of 1.0 ml/minute for 60 minutes.

Figure 6:
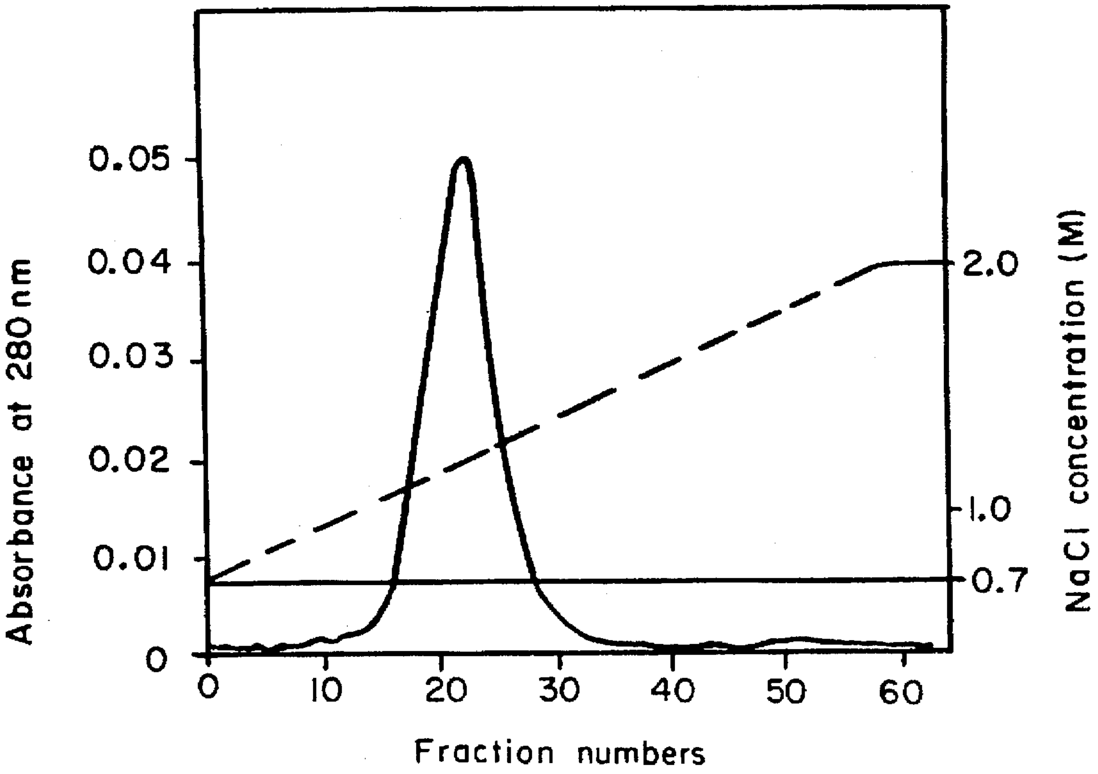
FIG. 6 shows an elution pattern obtained in Example 3.
Figure 7:
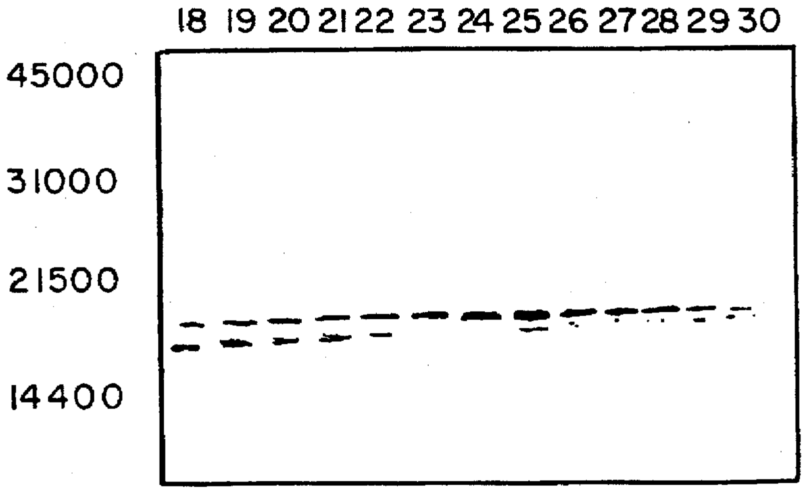
FIG. 7 shows electrophoresis patterns of SDS-PAGE obtained in Example 3.

The elution pattern is shown in FIG. 6. Referring to FIG. 6, the numbers on the ordinates indicate the absorbance at $OD_{280}$ and the concentration of NaCl in the gradient, and the numbers on the abscissa indicate the fraction number. The gradient elution was initiated at time 0. Fractions for every 0.1 minute were separately taken. The specific activity of the protein contained in these fractions and the amount of N38 recovered are shown in Table 2. The patterns of SDS-PAGE (12.5% polyacrylamide gel) of the respective fractions giving peaks are shown in FIG. 7.

TABLE 2

| | Protein (mg) | Hst-2 Activity (μg, bFGF equivalent) |
|---|---|---|
| Crude extract | 575 | 644 |
| Fractions not adsorbed to Q Sepharose | 480 | 461 |
| Heparin column elution fractions (23–25) | 0.22 | 43 |

b) Reverse C4 HPLC

Figure 8:
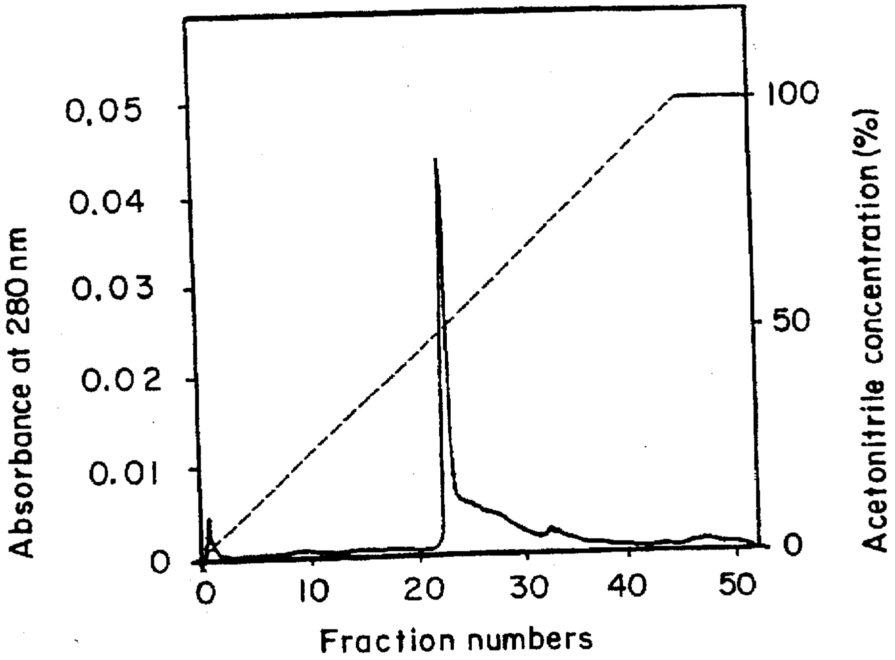
FIG. 8 shows an elution pattern obtained in Example 3.

About half (about 50 μg of protein) of the amount of fraction 22 eluted from the heparin HPLC column was applied to a reverse C4 column (VYDAC), and eluted with a linear gradient of 0 to 100% acetonitrile in the presence of 0.1% trifluoro acetic acid (TFA) to examine elution patterns. The elution was effected at a flow rate of 1 ml/minute for a gradient time of 45 minutes (FIG. 8).

Example 4

Biological Activity of N38

The activity of N38 obtained in Example 3-a) was assayed by measuring the DNA synthesis induction ability of mouse BALB/c3T3 cells based upon the uptake of [$^3$H] thymidine in accordance with the method of Sasada et al. [Sasada et al., *Mol. Cell. Biol.*, 8, 588–594 (1988)]. The results are shown in Table 2 given above.

Example 5

Amino Terminal Amino Acid Sequence

For 2.6 μg (about 130 pmol) of the purified protein of N38 obtained in Example 3-b), the N-terminal amino acid sequence was analyzed using a gas-phase protein sequencer (Model 473A, Applied Biosystems Inc.). Results thereof are shown in Table 3. These results revealed that the amino acid sequence of the amino terminal portion of N38 agreed with a sequence expected from the nucleotide sequence of the DNA of the expressed plasmid. The results proved that methionine derived from the translation initiation codon had been removed.

TABLE 3

| | PTH-Amino Acid | |
|---|---|---|
| Cycle | Amino Acid Residue | p mole |
| 1 | Pro | 36 |
| 2 | Ala | 42 |
| 3 | Gly | 32 |
| 4 | Thr | 12 |
| 5 | Arg | 4 |
| 6 | Ala | 25 |
| 7 | Asn | 16 |
| 8 | Asn | 16 |
| 9 | Thr | 8 |
| 10 | Leu | 16 |

Example 6

DNA Synthesis Induction Activity of N38

Figure 9:
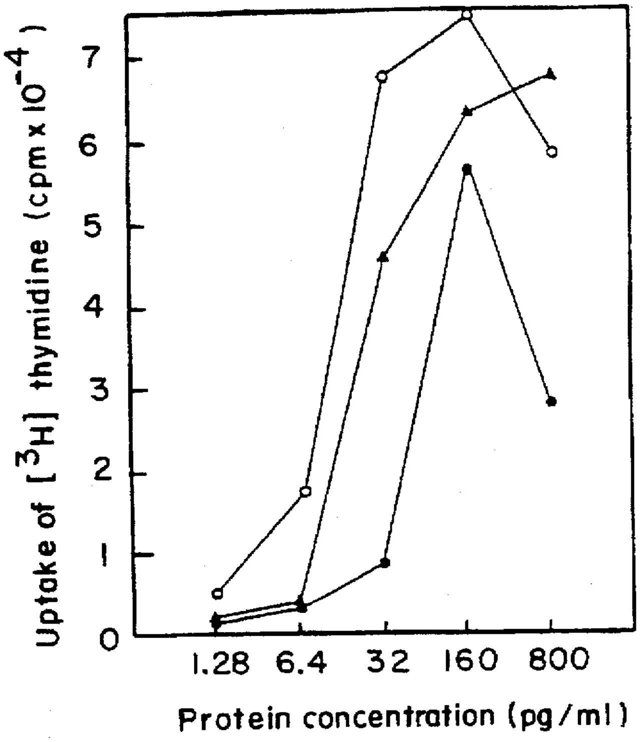
FIG. 9 shows results of DNA synthesis induction activity on mouse BALB/c3T3 cells, obtained in Example 6.

The DNA synthesis induction activity of the purified N38 obtained in Example 3-a) on mouse BALB/c3T3 cells was examined by the method described in Example 4, and results thereof are shown in FIG. 9. Referring to FIG. 9, open circles, closed circles and closed triangles show the results of bovine pituitary gland-derived FGF, the results of N38, and the results of N38 in the presence of heparin (5 μg/ml), respectively. The results shown in FIG. 9 revealed that N38 had activity similar to that of bovine pituitary gland-derived FGF (Takara Shuzo) and was enhanced in activity by addition of heparin.

Example 7

Transforming Activity of N38

1 μg/ml of N38 was added to mouse BALB/c3T3 A31 cells and cultivated. As a result, a transform cell-like morphological change was markedly observed. When heparin (5 μg/ml) was concurrently added, a similar change was observed by addition of 10 ng/ml of N38.

Example 8

Biological Activity of N63

The cells described in Example 2 collected from the 10-milliliter culture were suspended in 0.25 ml of 10 mM Tris-HCl (pH 7.4), 10 mM EDTA, 0.5M NaCl, 10% sucrose and 1 mM PMSF cooled with ice, and egg white lysozyme was added thereto to yield a concentration of 0.5 mg/ml. After standing in ice for 1 hour, the suspension was subjected to ultrasonic treatment (for 5 seconds, twice) and centrifugation (a Kubota cooled micro-centrifuge, at 15,000 rpm at 4° C. for 15 minutes) to obtain a supernatant as a cell extract. Using the cell extract, the activity of N63 was assayed according to the method described in Example 4. Results thereof showed that N63 was produced in an amount of about 60 μg/ml as the FGF equivalent.

Example 9

MK-CSF Activity of N38

Bone marrow cells collected from the femurs of BALB/c mice (female, 7 weeks old) were suspended in IMDM medium (Iscove's Modification of Dulbecco's Medium) (Flow) containing 10% fetal calf serum (FCS) at $2\times10^5$ cells/ml, and incubated on a plastic plate at 37° C. for 45 minutes. Non-adhesive cells were collected and washed with IMDM medium to remove the serum. These non-adhesive bone marrow cells ($1\times10^5$ cells/ml) were suspended in IMDM medium containing Neutridoma-sp (Boehringer Mannheim), and a 96-well flat-bottomed plate (NUNC) was inoculated with 200 μl/well of the suspension. Then, N38 was added at various concentrations, alone or together with heparin (20 μg/ml).

Figure 10:
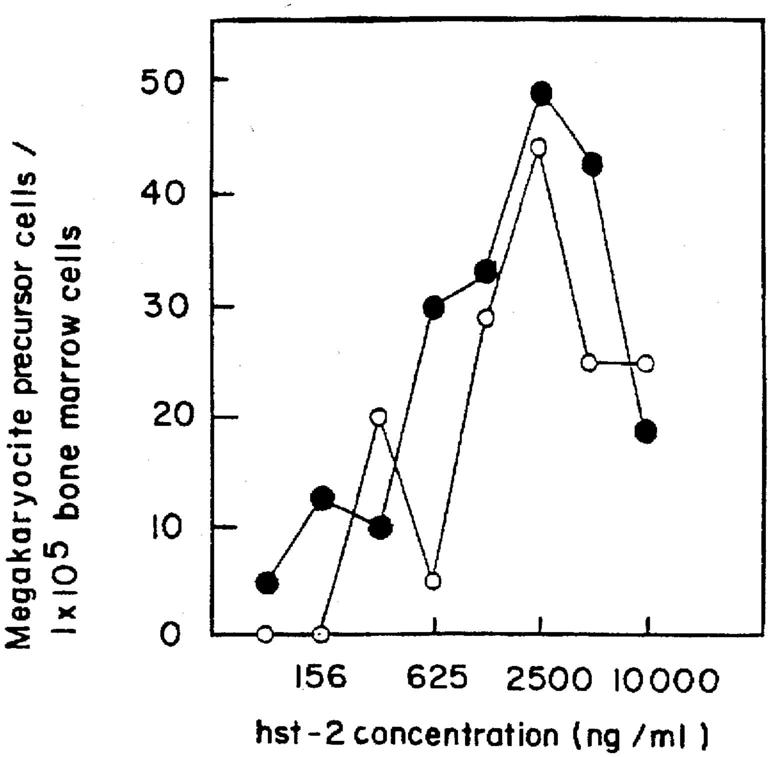
FIG. 10 shows results of the megakaryocyte precursor cell growth promoting activity test obtained in Example 9.

After cultivation at 37° C. for 7 days, 50 μl of 5% glutaraldehyde (Wako Pure Chemical Industries) was added, and the plate was centrifuged at 2,000 rpm for 5 minutes to fix the cells. The plate was briefly washed with 0.1M phosphate buffer (pH 6.0), followed by acetylcholine staining. Namely, 30 mg of acetylthiocholine iodide (SIGMA) was dissolved in 45 ml of 0.1M phosphate buffer, and then, 6 ml of 30 mM copper sulfate, 3 ml of 0.1M sodium citrate and 6 ml of 5 mM potassium ferricyanide were added thereto to prepare a staining solution at the time of use. To each well was added 200 μl of the solution, and staining was carried out at room temperature for 6 hours. After washing with 0.1M phosphate buffer, the number of megakaryocytes was counted under a inverted microscope. As shown in FIG. 10, N38 stimulated the proliferation of megakaryocyte precursor cells in the mouse bone marrow, in a dose dependent manner.

Example 10

Growth Promoting Activity of N38 on Endothelial Cells

Figure 11:
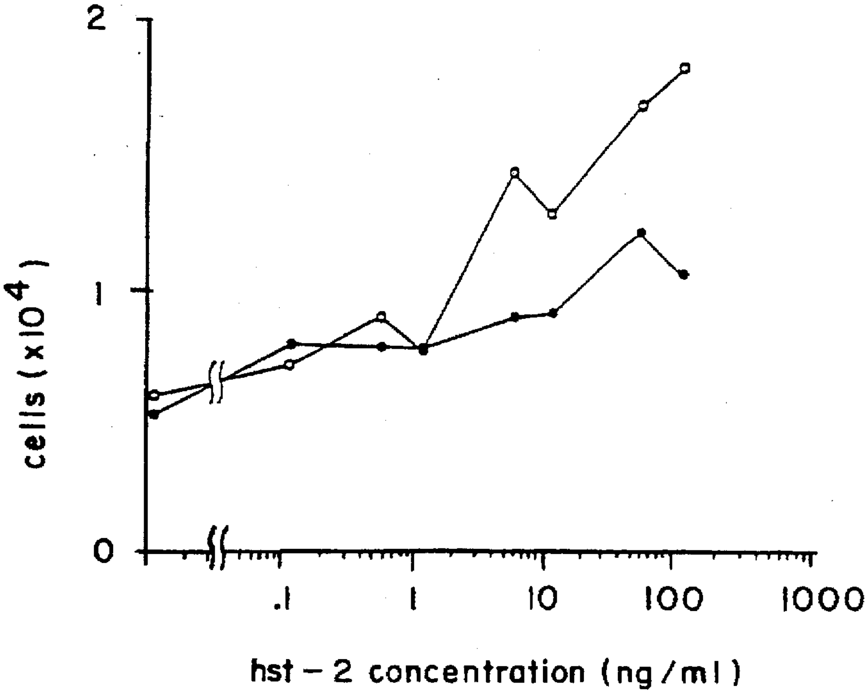
FIG. 11 shows results of the cell growth promoting activity test obtained in Example 10.

A Linbro dish (Flow) was inoculated with HUVE cells suspended in modified MCDB131 (Kurabo Industries Ltd.) containing 2% FCS (MBA) to give $5\times10^3$ cells/well. The next day, N38 was added at various concentrations, alone or together with heparin (5 μg/ml). After 5 days, the number of cells was counted. Results thereof are shown in FIG. 11. A similar operation was conducted with the exception that the medium was replaced by the above-mentioned medium to which epidermal growth factor (EGF) was added so as to give a concentration of 10 ng/ml. Results thereof are shown in FIG. 12.

Figure 12:
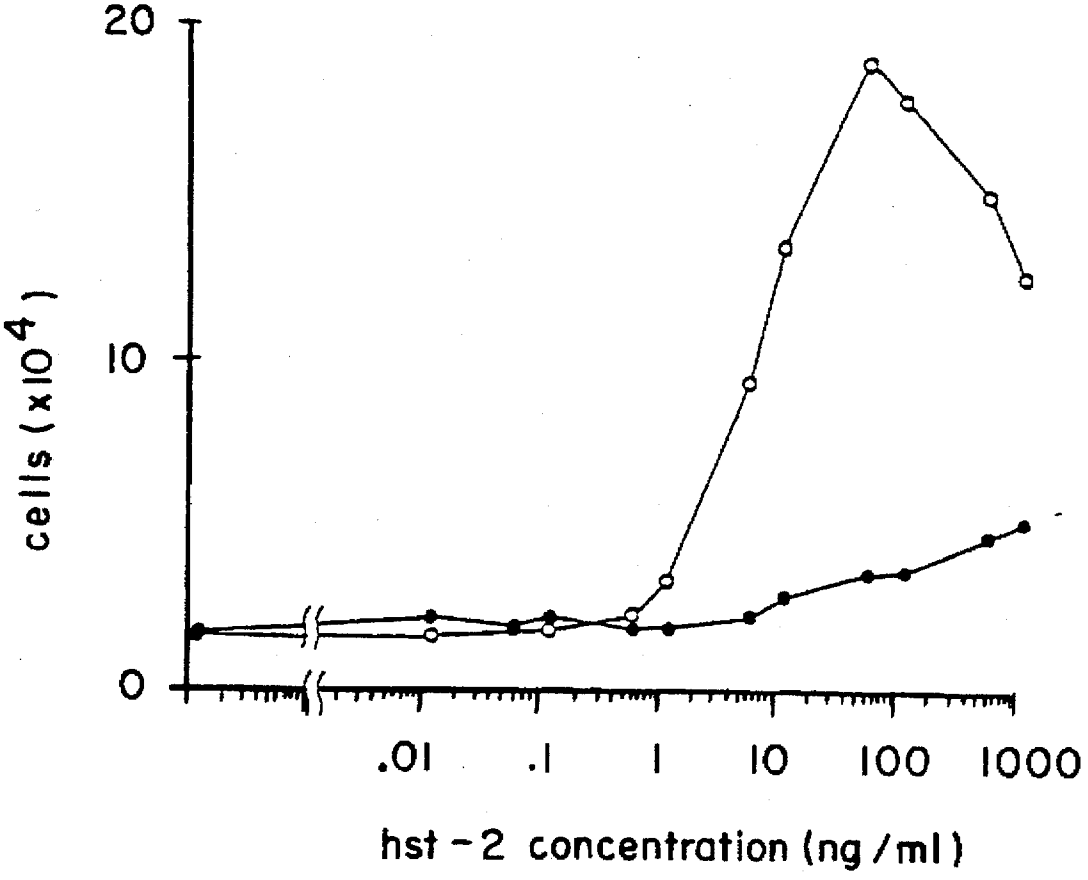
FIG. 12 shows results of the cell growth promoting activity test obtained in Example 10.

Referring to FIGS. 11 and 12, closed circles (●) and open circles (○) indicate the results of N38 alone and the results of N38 in the presence of heparin (5 μg/ml), respectively. As shown in FIG. 11, the results proved that N38 had cell growth promoting activity on HUVE cells and this activity was enhanced by addition of heparin. Further, as shown in FIG. 12, the results revealed that the difference between both in cell growth promoting activity became more remarkable for 2% FCS-containing modified MCDB131 medium supplemented with 10 ng/ml of EGF.

Formulation Example 1

N38 prepared in Example 3 is dialyzed overnight against 50 mM citrate buffer (pH 5.0), followed by preparation of a solution having a concentration of 500 μg/ml. The solution is sterilized through filtration, and 1 ml of the resulting solution is poured into each vial to prepare a preparation for injection.

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 170 amino acids
( B ) TYPE: amino acid
( D ) TOPOLOGY: linear ( i i ) MOLECULE TYPE: protein ( x i ) SEQUENCE DESCRIPTION: SEQ ID NO:1:

```
Pro Ala Gly Thr Arg Ala Asn Asn Thr Leu Leu Asp Ser Arg Gly Trp
1               5                   10                  15

Gly Thr Leu Leu Ser Arg Ser Arg Ala Gly Leu Ala Gly Glu Ile Ala
            20                  25                  30

Gly Val Asn Trp Glu Ser Gly Tyr Leu Val Gly Ile Lys Arg Gln Arg
        35                  40                  45

Arg Leu Tyr Cys Asn Val Gly Ile Gly Phe His Leu Gln Val Leu Pro
    50                  55                  60

Asp Gly Arg Ile Ser Gly Thr His Glu Glu Asn Pro Tyr Ser Leu Leu
65                  70                  75                  80

Glu Ile Ser Thr Val Glu Arg Gly Val Val Ser Leu Phe Gly Val Arg
                85                  90                  95

Ser Ala Leu Phe Val Ala Met Asn Ser Lys Gly Arg Leu Tyr Ala Thr
            100                 105                 110

Pro Ser Phe Gln Glu Glu Cys Lys Phe Arg Glu Thr Leu Leu Pro Asn
        115                 120                 125

Asn Tyr Asn Ala Tyr Glu Ser Asp Leu Tyr Gln Gly Thr Tyr Ile Ala
    130                 135                 140

Leu Ser Lys Tyr Gly Arg Val Lys Arg Gly Ser Lys Val Ser Pro Ile
145                 150                 155                 160

Met Thr Val Thr His Phe Leu Pro Arg Ile
                165                 170
```

( 2 ) INFORMATION FOR SEQ ID NO:2:

( i ) SEQUENCE CHARACTERISTICS:
( A ) LENGTH: 171 amino acids

-continued (B) TYPE: amino acid
(D) TOPOLOGY: linear (ii) MOLECULE TYPE: protein (xi) SEQUENCE DESCRIPTION: SEQ ID NO:2:

Met Pro Ala Gly Thr Arg Ala Asn Asn Thr Leu Leu Asp Ser Arg Gly
1 5 10 15

Trp Gly Thr Leu Leu Ser Arg Ser Arg Ala Gly Leu Ala Gly Glu Ile
20 25 30

Ala Gly Val Asn Trp Glu Ser Gly Tyr Leu Val Gly Ile Lys Arg Gln
35 40 45

Arg Arg Leu Tyr Cys Asn Val Gly Ile Gly Phe His Leu Gln Val Leu
50 55 60

Pro Asp Gly Arg Ile Ser Gly Thr His Glu Glu Asn Pro Tyr Ser Leu
65 70 75 80

Leu Glu Ile Ser Thr Val Glu Arg Gly Val Val Ser Leu Phe Gly Val
85 90 95

Arg Ser Ala Leu Phe Val Ala Met Asn Ser Lys Gly Arg Leu Tyr Ala
100 105 110

Thr Pro Ser Phe Gln Glu Glu Cys Lys Phe Arg Glu Thr Leu Leu Pro
115 120 125

Asn Asn Tyr Asn Ala Tyr Glu Ser Asp Leu Tyr Gln Gly Thr Tyr Ile
130 135 140

Ala Leu Ser Lys Tyr Gly Arg Val Lys Arg Gly Ser Lys Val Ser Pro
145 150 155 160

Ile Met Thr Val Thr His Phe Leu Pro Arg Ile
165 170

(2) INFORMATION FOR SEQ ID NO:3:

(i) SEQUENCE CHARACTERISTICS:
(A) LENGTH: 145 amino acids
(B) TYPE: amino acid
(D) TOPOLOGY: linear (ii) MOLECULE TYPE: protein (xi) SEQUENCE DESCRIPTION: SEQ ID NO:3:

Gly Leu Ala Gly Glu Ile Ala Gly Val Asn Trp Glu Ser Gly Tyr Leu
1 5 10 15

Val Gly Ile Lys Arg Gln Arg Arg Leu Tyr Cys Asn Val Gly Ile Gly
20 25 30

Phe His Leu Gln Val Leu Pro Asp Gly Arg Ile Ser Gly Thr His Glu
35 40 45

Glu Asn Pro Tyr Ser Leu Leu Glu Ile Ser Thr Val Glu Arg Gly Val
50 55 60

Val Ser Leu Phe Gly Val Arg Ser Ala Leu Phe Val Ala Met Asn Ser
65 70 75 80

Lys Gly Arg Leu Tyr Ala Thr Pro Ser Phe Gln Glu Glu Cys Lys Phe
85 90 95

Arg Glu Thr Leu Leu Pro Asn Asn Tyr Asn Ala Tyr Glu Ser Asp Leu
100 105 110

Tyr Gln Gly Thr Tyr Ile Ala Leu Ser Lys Tyr Gly Arg Val Lys Arg
115 120 125

Gly Ser Lys Val Ser Pro Ile Met Thr Val Thr His Phe Leu Pro Arg
130 135 140

Ile

145

( 2 ) INFORMATION FOR SEQ ID NO:4:

( i ) SEQUENCE CHARACTERISTICS:
( A ) LENGTH: 146 amino acids
( B ) TYPE: amino acid
( D ) TOPOLOGY: linear ( i i ) MOLECULE TYPE: protein ( x i ) SEQUENCE DESCRIPTION: SEQ ID NO:4:

Met Gly Leu Ala Gly Glu Ile Ala Gly Val Asn Trp Glu Ser Gly Tyr
1 5 10 15

Leu Val Gly Ile Lys Arg Gln Arg Arg Leu Tyr Cys Asn Val Gly Ile
20 25 30

Gly Phe His Leu Gln Val Leu Pro Asp Gly Arg Ile Ser Gly Thr His
35 40 45

Glu Glu Asn Pro Tyr Ser Leu Leu Glu Ile Ser Thr Val Glu Arg Gly
50 55 60

Val Val Ser Leu Phe Gly Val Arg Ser Ala Leu Phe Val Ala Met Asn
65 70 75 80

Ser Lys Gly Arg Leu Tyr Ala Thr Pro Ser Phe Gln Glu Glu Cys Lys
85 90 95

Phe Arg Glu Thr Leu Leu Pro Asn Asn Tyr Asn Ala Tyr Glu Ser Asp
100 105 110

Leu Tyr Gln Gly Thr Tyr Ile Ala Leu Ser Lys Tyr Gly Arg Val Lys
115 120 125

Arg Gly Ser Lys Val Ser Pro Ile Met Thr Val Thr His Phe Leu Pro
130 135 140

Arg Ile
145

( 2 ) INFORMATION FOR SEQ ID NO:5:

( i ) SEQUENCE CHARACTERISTICS:
( A ) LENGTH: 207 amino acids
( B ) TYPE: amino acid
( D ) TOPOLOGY: linear ( i i ) MOLECULE TYPE: protein ( x i ) SEQUENCE DESCRIPTION: SEQ ID NO:5:

Ala Leu Gly Gln Lys Leu Phe Ile Thr Met Ser Arg Gly Ala Gly Arg
1 5 10 15

Leu Gln Gly Thr Leu Trp Ala Leu Val Phe Leu Gly Ile Leu Val Gly
20 25 30

Met Val Val Pro Ser Pro Ala Gly Thr Arg Ala Asn Asn Thr Leu Leu
35 40 45

Asp Ser Arg Gly Trp Gly Thr Leu Leu Ser Arg Ser Arg Ala Gly Leu
50 55 60

Ala Gly Glu Ile Ala Gly Val Asn Trp Glu Ser Gly Tyr Leu Val Gly
65 70 75 80

Ile Lys Arg Gln Arg Arg Leu Tyr Cys Asn Val Gly Ile Gly Phe His
85 90 95

Leu Gln Val Leu Pro Asp Gly Arg Ile Ser Gly Thr His Glu Glu Asn
100 105 110

Pro Tyr Ser Leu Leu Glu Ile Ser Thr Val Glu Arg Gly Val Val Ser
115 120 125

-continued

Leu Phe Gly Val Arg Ser Ala Leu Phe Val Ala Met Asn Ser Lys Gly
130 135 140

Arg Leu Tyr Ala Thr Pro Ser Phe Gln Glu Glu Cys Lys Phe Arg Glu
145 150 155 160

Thr Leu Leu Pro Asn Asn Tyr Asn Ala Tyr Glu Ser Asp Leu Tyr Gln
165 170 175

Gly Thr Tyr Ile Ala Leu Ser Lys Tyr Gly Arg Val Lys Arg Gly Ser
180 185 190

Lys Val Ser Pro Ile Met Thr Val Thr His Phe Leu Pro Arg Ile
195 200 205

( 2 ) INFORMATION FOR SEQ ID NO:6:

( i ) SEQUENCE CHARACTERISTICS:
( A ) LENGTH: 208 amino acids
( B ) TYPE: amino acid
( D ) TOPOLOGY: linear ( i i ) MOLECULE TYPE: protein ( x i ) SEQUENCE DESCRIPTION: SEQ ID NO:6:

Met Ala Leu Gly Gln Lys Leu Phe Ile Thr Met Ser Arg Gly Ala Gly
1 5 10 15

Arg Leu Gln Gly Thr Leu Trp Ala Leu Val Phe Leu Gly Ile Leu Val
20 25 30

Gly Met Val Val Pro Ser Pro Ala Gly Thr Arg Ala Asn Asn Thr Leu
35 40 45

Leu Asp Ser Arg Gly Trp Gly Thr Leu Leu Ser Arg Ser Arg Ala Gly
50 55 60

Leu Ala Gly Glu Ile Ala Gly Val Asn Trp Glu Ser Gly Tyr Leu Val
65 70 75 80

Gly Ile Lys Arg Gln Arg Arg Leu Tyr Cys Asn Val Gly Ile Gly Phe
85 90 95

His Leu Gln Val Leu Pro Asp Gly Arg Ile Ser Gly Thr His Glu Glu
100 105 110

Asn Pro Tyr Ser Leu Leu Glu Ile Ser Thr Val Glu Arg Gly Val Val
115 120 125

Ser Leu Phe Gly Val Arg Ser Ala Leu Phe Val Ala Met Asn Ser Lys
130 135 140

Gly Arg Leu Tyr Ala Thr Pro Ser Phe Gln Glu Glu Cys Lys Phe Arg
145 150 155 160

Glu Thr Leu Leu Pro Asn Asn Tyr Asn Ala Tyr Glu Ser Asp Leu Tyr
165 170 175

Gln Gly Thr Tyr Ile Ala Leu Ser Lys Tyr Gly Arg Val Lys Arg Gly
180 185 190

Ser Lys Val Ser Pro Ile Met Thr Val Thr His Phe Leu Pro Arg Ile
195 200 205

( 2 ) INFORMATION FOR SEQ ID NO:7:

( i ) SEQUENCE CHARACTERISTICS:
( A ) LENGTH: 174 amino acids
( B ) TYPE: amino acid
( D ) TOPOLOGY: linear ( i i ) MOLECULE TYPE: protein ( x i ) SEQUENCE DESCRIPTION: SEQ ID NO:7:

Val Val Pro Ser Pro Ala Gly Thr Arg Ala Asn Asn Thr Leu Leu Asp

-continued 1 5 10 15

Ser Arg Gly Trp Gly Thr Leu Leu Ser Arg Ser Arg Ala Gly Leu Ala
20 25 30

Gly Glu Ile Ala Gly Val Asn Trp Glu Ser Gly Tyr Leu Val Gly Ile
35 40 45

Lys Arg Gln Arg Arg Leu Tyr Cys Asn Val Gly Ile Gly Phe His Leu
50 55 60

Gln Val Leu Pro Asp Gly Arg Ile Ser Gly Thr His Glu Glu Asn Pro
65 70 75 80

Tyr Ser Leu Leu Glu Ile Ser Thr Val Glu Arg Gly Val Val Ser Leu
85 90 95

Phe Gly Val Arg Ser Ala Leu Phe Val Ala Met Asn Ser Lys Gly Arg
100 105 110

Leu Tyr Ala Thr Pro Ser Phe Gln Glu Glu Cys Lys Phe Arg Glu Thr
115 120 125

Leu Leu Pro Asn Asn Tyr Asn Ala Tyr Glu Ser Asp Leu Tyr Gln Gly
130 135 140

Thr Tyr Ile Ala Leu Ser Lys Tyr Gly Arg Val Lys Arg Gly Ser Lys
145 150 155 160

Val Ser Pro Ile Met Thr Val Thr His Phe Leu Pro Arg Ile
165 170

( 2 ) INFORMATION FOR SEQ ID NO:8:

( i ) SEQUENCE CHARACTERISTICS:
( A ) LENGTH: 175 amino acids
( B ) TYPE: amino acid
( D ) TOPOLOGY: linear ( i i ) MOLECULE TYPE: protein ( x i ) SEQUENCE DESCRIPTION: SEQ ID NO:8:

Met Val Val Pro Ser Pro Ala Gly Thr Arg Ala Asn Asn Thr Leu Leu
1 5 10 15

Asp Ser Arg Gly Trp Gly Thr Leu Leu Ser Arg Ser Arg Ala Gly Leu
20 25 30

Ala Gly Glu Ile Ala Gly Val Asn Trp Glu Ser Gly Tyr Leu Val Gly
35 40 45

Ile Lys Arg Gln Arg Arg Leu Tyr Cys Asn Val Gly Ile Gly Phe His
50 55 60

Leu Gln Val Leu Pro Asp Gly Arg Ile Ser Gly Thr His Glu Glu Asn
65 70 75 80

Pro Tyr Ser Leu Leu Glu Ile Ser Thr Val Glu Arg Gly Val Val Ser
85 90 95

Leu Phe Gly Val Arg Ser Ala Leu Phe Val Ala Met Asn Ser Lys Gly
100 105 110

Arg Leu Tyr Ala Thr Pro Ser Phe Gln Glu Glu Cys Lys Phe Arg Glu
115 120 125

Thr Leu Leu Pro Asn Asn Tyr Asn Ala Tyr Glu Ser Asp Leu Tyr Gln
130 135 140

Gly Thr Tyr Ile Ala Leu Ser Lys Tyr Gly Arg Val Lys Arg Gly Ser
145 150 155 160

Lys Val Ser Pro Ile Met Thr Val Thr His Phe Leu Pro Arg Ile
165 170 175

( 2 ) INFORMATION FOR SEQ ID NO:9:

-continued ( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: Other nucleic acid, synthetic DNA ( i v ) ANTI-SENSE: NO ( x i ) SEQUENCE DESCRIPTION: SEQ ID NO:9:

GGGCATATGC CTGCA 15

( 2 ) INFORMATION FOR SEQ ID NO:10:

( i ) SEQUENCE CHARACTERISTICS:
( A ) LENGTH: 11 base pairs
( B ) TYPE: nucleic acid
( C ) STRANDEDNESS: single
( D ) TOPOLOGY: linear ( i i ) MOLECULE TYPE: Other nucleic acid, synthetic DNA ( i v ) ANTI-SENSE: YES ( x i ) SEQUENCE DESCRIPTION: SEQ ID NO:10:

GGCATATGCC C 11

What is claimed is:

1. A polypeptide represented by the following amino acid sequence:

$(Met)_n$X Leu Ala Gly Glu Ile Ala Gly Val Asn Trp Glu Ser

Gly Tyr Leu Val Gly Ile Lys Arg Gln Arg Arg Leu Tyr Cys Asn

Val Gly Ile Gly Phe His Leu Gln Val Leu Pro Asp Gly Arg Ile

Ser Gly Thr His Glu Glu Asn Pro Tyr Ser Leu Leu Glu Ile Ser

Thr Val Glu Arg Gly Val Val Ser Leu Phe Gly Val Arg Ser Ala

Leu Phe Val Ala Met Asn Ser Lys Gly Arg Leu Tyr Ala Thr Pro

Ser Phe Gln Glu Glu Cys Lys Phe Arg Glu Thr Leu Leu Pro Asn

Asn Tyr Asn Ala Tyr Glu Ser Asp Leu Tyr Gln Gly Thr Tyr Ile

Ala Leu Ser Lys Tyr Gly Arg Val Lys Arg Gly Ser Lys Val Ser

Pro Ile Met Thr Val Thr His Phe Leu Pro Arg Ile wherein n is 0 or 1 and X represents X', wherein X' has the sequence Pro Ala Gly Thr Arg Ala Asn Asn Thr Leu Leu Asp Ser Arg Gly Trp Gly Thr Leu Leu Set Arg Ser Arg Ala Gly, or is a fragment of X' that has at least one amino acid from the C-terminus of X'; and which has heparin-binding secretory transforming factor 2 (hst-2) activity as determined by measuring the stimulation of DNA synthesis by BALB/c3T3 cells or growth promotion of vascular endothelial cells; wherein the polypeptide has the amino acid sequence of SEQ ID NO: 1 when X is X' and n=0, and the polypeptide has the amino acid sequence of SEQ ID NO: 2 when X is X' and n=1.

2. The polypeptide as claimed in claim 1, wherein X represents Pro Ala Gly Thr Arg Ala Asn Asn Thr Leu Leu Asp Ser Arg Gly Trp Gly Thr Leu Leu Ser Arg Ser Arg Ala Gly, wherein when n is 0, the polypeptide is SEQ ID NO:1 and when n is 1, the polypeptide is SEQ ID NO:2.

3. The polypeptide as claimed in claim 1, wherein X represents Gly, wherein when n is 0, the polypeptide is SEQ ID NO:3, and when n is 1, the polypeptide is SEQ ID NO:4.

4. The polypeptide as claimed in claim 1, wherein said polypeptide has amino acid sequence of SEQ ID NO:1.

5. The polypeptide as claimed in claim 1, wherein said polypeptide has amino acid sequence of SEQ ID NO:3.

6. A pharmaceutical composition comprising an effective amount of the polypeptide as claimed in any one of claims 1 to 5 and a pharmacologically acceptable carrier.

7. The pharmaceutical composition as claimed in claim 6, wherein said composition is a composition for promoting an increase in the number of platelets in a mammal.

8. A kit of pharmaceutical preparations for increasing platelets and treating a disease in a mammal, which comprises a pharmaceutical composition as claimed in claim 6 in lyophillized form in a container and an anticancer agent.

9. A polypeptide represented by the following amino acid sequence:

(Met)n XLeu Ala Gly Glu Ile Ala Gly Val Asn Trp Glu Ser

Gly Tyr Leu Val Gly Ile Lys Arg Gln Arg Arg Leu Tyr Cys Asn

Val Gly Ile Gly Phe His Leu Gln Val Leu Pro Asp Gly Arg Ile

Ser Gly Thr His Glu Glu Asn Pro Tyr Ser Leu Leu Glu Ile Ser

-continued

Thr Val Glu Arg Gly Val Val Ser Leu Phe Gly Val Arg Ser Ala

Leu Phe Val Ala Met Asn Ser Lys Gly Arg Leu Tyr Ala Thr Pro

Ser Phe Gln Glu Glu Cys Lys Phe Arg Glu Thr Leu Leu Pro Asn

Asn Tyr Asn Ala Tyr Glu Ser Asp Leu Tyr Gln Gly Thr Tyr Ile

Ala Leu Ser Lys Tyr Gly Arg Val Lys Arg Gly Ser Lys Val Ser

Pro Ile Met Thr Val Thr His Phe Leu Pro Arg Ile wherein n is 0 or 1 and X represents X', wherein X' has the sequence Pro Ala Gly Thr Arg Ala Asn Asn Thr Leu Leu Asp Ser Arg Gly Trp Gly Thr Leu Leu Ser Arg Ser Arg Ala Gly, or a fragment of X', wherein 1 to 25 successive and no acid residues are deleted from the N-terminus of X', and wherein said polypeptide has heparin-binding secretory transforming factor 2 (hst-2) activity as determined by measuring the stimulation of DNA synthesis by BALB/c3T3 cells or growth promotion of vascular endothelial cells, and wherein when X is X' said polypeptide is SEQ ID NO:1 when n=0, and said polypeptide is SEQ ID NO:2, when n=1.

10. A method for producing the polypeptide of claim 1 comprising cultivating a transformant carrying a vector containing a recombinant DNA encoding the polypeptide of claim 1 in a medium for sufficient time under sufficient conditions to express said polypeptide and harvesting said polypeptide.

* * * * *